(12) United States Patent
Korpela et al.

(10) Patent No.: US 8,247,204 B2
(45) Date of Patent: Aug. 21, 2012

(54) MAGNETIC ENRICHMENT METHOD, A REACTOR UNIT FOR MICRO PARTICLES AND A MAGNET UNIT

(75) Inventors: Matti Korpela, Naantali (FI); Kenneth Rundt, Turku (FI)

(73) Assignee: BioControl Systems, Inc., Bellevue, WA (US)

( * ) Notice: Subject to any disclaimer, the term of this patent is extended or adjusted under 35 U.S.C. 154(b) by 1186 days.

(21) Appl. No.: 10/576,298

(22) PCT Filed: Oct. 20, 2004

(86) PCT No.: PCT/IB2004/003432
§ 371 (c)(1),
(2), (4) Date: Feb. 15, 2007

(87) PCT Pub. No.: WO2005/037440
PCT Pub. Date: Apr. 28, 2005

(65) Prior Publication Data
US 2008/0118967 A1   May 22, 2008

(30) Foreign Application Priority Data

Oct. 20, 2003  (FI) ..................................... 20031535
Feb. 2, 2004  (FI) ..................................... 20040159

(51) Int. Cl.
*C12N 13/00*  (2006.01)

(52) U.S. Cl. ................... 435/173.9; 435/173.1; 435/261; 210/695; 210/222; 335/295; 335/298

(58) Field of Classification Search ............... 435/173.1, 435/173.9, 261; 335/295
See application file for complete search history.

(56) References Cited

U.S. PATENT DOCUMENTS

| | | | |
|---|---|---|---|
| 2,517,325 A * | 8/1950 | Lamb ............................... | 600/11 |
| 3,223,898 A * | 12/1965 | Bey ................................. | 335/295 |
| 3,985,649 A | 10/1976 | Eddelman .................... | 210/42 S |
| 4,272,510 A | 6/1981 | Smith et al. .................... | 427/47 |
| 4,649,116 A | 3/1987 | Daty et al. .................... | 435/287 |
| 4,738,773 A | 4/1988 | Müller-Ruchholtz et al. ............................. | 209/214 |
| 4,751,053 A | 6/1988 | Dodin et al. .................. | 422/101 |
| 5,053,344 A | 10/1991 | Zborowski et al. ............ | 436/177 |
| 5,567,326 A | 10/1996 | Ekenberg et al. ............. | 210/695 |
| 5,837,144 A | 11/1998 | Bienhaus et al. ............. | 210/695 |
| 5,942,124 A | 8/1999 | Tuunanen .................... | 210/695 |
| 5,972,721 A | 10/1999 | Bruno et al. .................. | 436/526 |
| 6,020,211 A | 2/2000 | Tuunanen .................... | 436/526 |
| 6,040,192 A | 3/2000 | Tuunanen .................... | 436/177 |
| 6,065,605 A | 5/2000 | Korpela et al. ............... | 209/216 |
| 6,126,835 A * | 10/2000 | Barbera-Guillem et al. . | 210/695 |
| 6,143,577 A | 11/2000 | Bisconte Sconte De Saint Julien .......................... | 436/526 |
| 6,159,689 A | 12/2000 | Parton ............................. | 435/6 |
| 6,207,463 B1 | 3/2001 | Tuunanen .................... | 436/526 |
| 6,403,038 B1 | 6/2002 | Heermann .................... | 422/101 |
| 6,409,925 B1 | 6/2002 | Gombinsky et al. .......... | 210/695 |
| 6,448,092 B1 | 9/2002 | Tuunanen .................... | 436/526 |
| 6,468,810 B1 | 10/2002 | Korpela ........................ | 436/526 |
| 6,596,162 B2 | 7/2003 | Tuunanen .................... | 210/222 |
| 2001/0022948 A1 | 9/2001 | Tuunanen ..................... | 422/99 |
| 2003/0062314 A1 | 4/2003 | Davidson et al. ............. | 210/695 |

FOREIGN PATENT DOCUMENTS

| | | |
|---|---|---|
| DE | 100 57 396 C1 | 4/2002 |
| DE | 100 63 984 A1 | 6/2002 |
| EP | 0 842 704 A1 | 5/1998 |
| EP | 0 787 296 B1 | 3/2001 |
| EP | 1 162 444 A1 | 12/2001 |
| EP | 1 058 851 B1 | 7/2005 |
| WO | 87/05536 | 9/1987 |
| WO | 01/60967 | 8/2001 |
| WO | 03/044537 A1 | 5/2003 |

* cited by examiner

*Primary Examiner* — Allison Ford
*Assistant Examiner* — Susan E Fernandez

(57) ABSTRACT

Magnetic enrichment method, wherein the desired biological component is collected from a solution, which component is thereafter enriched in a liquid in such a manner that by means of the micro particles attached to the magnet or attached by means of at least one magnet at least one biological component is collected in a closed reactor vessel. Thereafter at least one biological component is enriched in such a manner that the desired component is released to the solution. The reactor unit is a closed vessel, wherein the prevailing conditions are controllable. The shape and the location of the magnet unit in the reactor unit are adjusted in a preferable manner to collect the desired biological component.

19 Claims, 14 Drawing Sheets

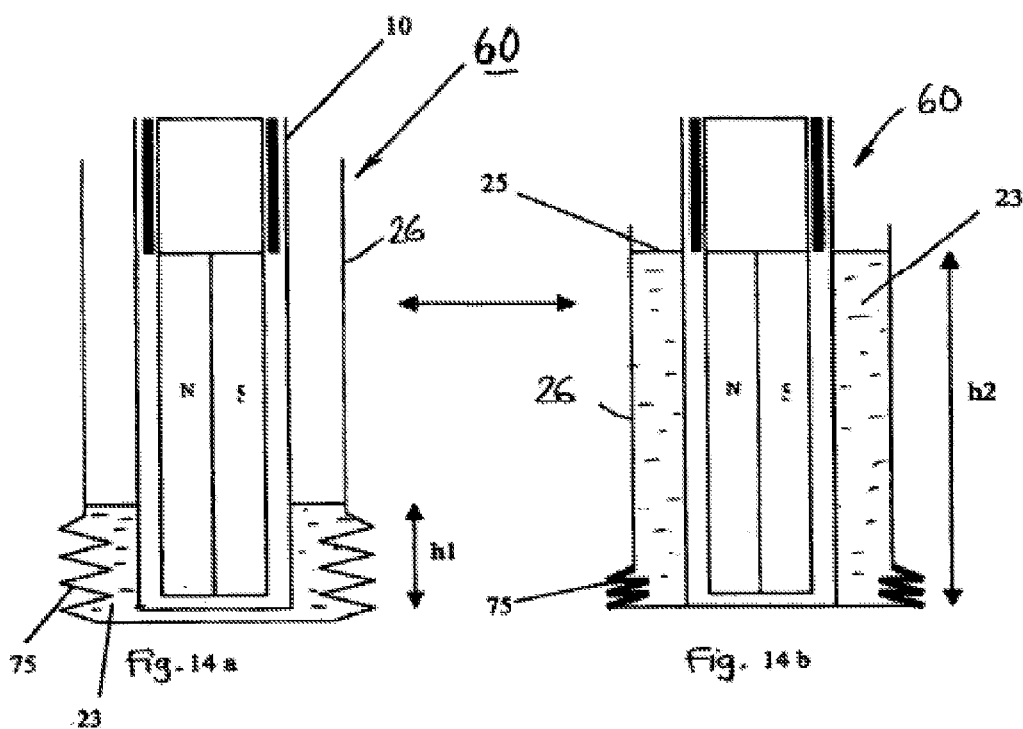

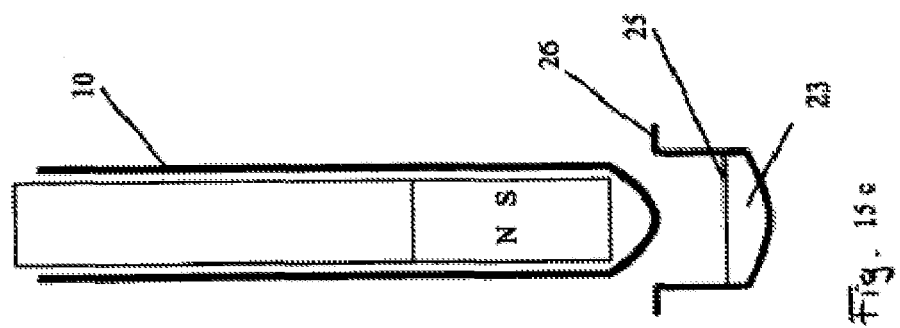
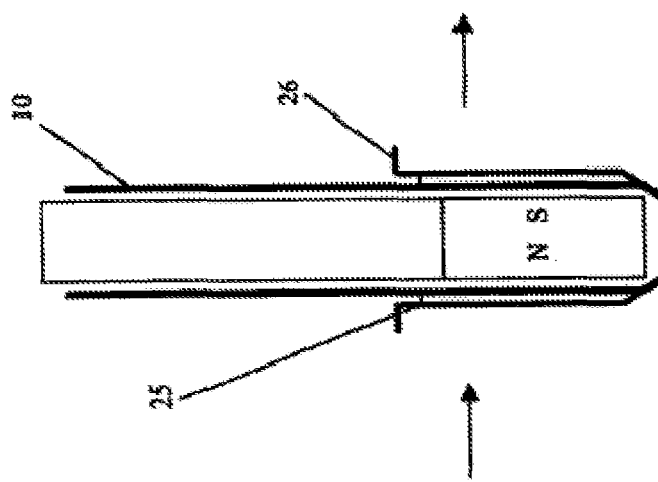
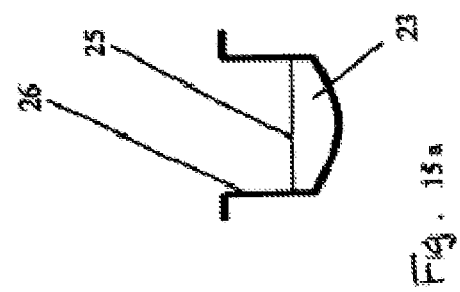

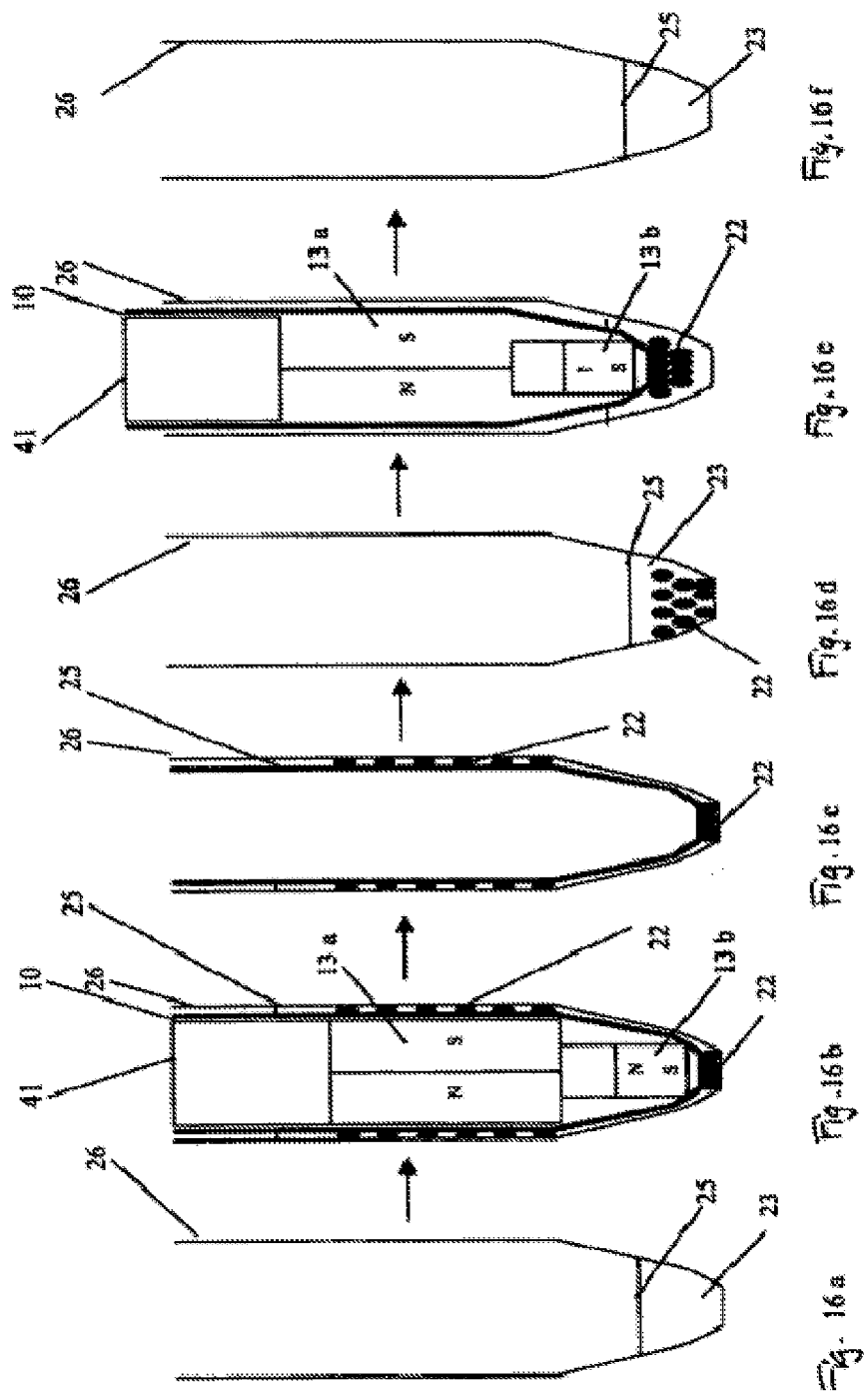

MAGNETIC ENRICHMENT METHOD, A REACTOR UNIT FOR MICRO PARTICLES AND A MAGNET UNIT

This application is a 371 of international application PCT/IB2004/003432, which claims priority based on Finnish patent application Nos. FI-20031535 filed Oct. 20, 2003, and FI-20040159 filed Feb. 2, 2004, which are incorporated herein by reference.

FIELD OF THE INVENTION

The invention relates to a magnetic enrichment method, whereby the desired biological component is collected from a solution by means of a magnet, which component is thereafter concentrated in a liquid. The invention further relates to a reactor unit for micro particles and a magnet unit.

BACKGROUND OF THE INVENTION

Magnetic transfer method refers to all action related to the movement of particles by means of magnetism, such as assorting, collecting, transferring, mixing and dosing within a solution or from one solution to another.

Particles, micro particles or magnetic particles refer to all such small particles that have their diameter in the range of micrometers, and that can be moved by means of magnetism. There are various known particles that are transferable with a magnet and also applications, where they are used, greatly vary. For example, particles used in microbiology usually have a size of 0.01-100 µm, most commonly 0.05-10 µm. Such known particles are, for example, particles containing ferromagnetic, paramagnetic or supra-magnetic material. Particles can also be magnetic themselves, in which case they can be moved by means of any ferromagnetic object.

In a device intended for to treat micro particles, there is a unit exploiting magnetism that is hereinafter referred to as a magnet. It can be a permanent magnet or an electrical magnet attracting particles, such as ferromagnetic, paramagnetic or super-paramagnetic particles, or a ferromagnetic object that is not magnetic itself, but still attracts magnetic particles.

A magnet is usually preferably a rounded bar magnet. It can also be a bar of another shape. However, a magnet does not need to be a bar at all. It can also be short and broad or an object of any shape. A magnet can also consist of one or more objects, such as magnets or ferromagnetic objects. The magnet can also be connected to objects consisting of non-ferromagnetic material.

There has to be a shield covering the magnet, protecting the magnet from various harmful conditions and enabling the treatment of micro particles, such as binding and release. The structure of the shield may greatly vary for it can be, for example, a thin membrane consisting of flexible or stretchy material or even a cup consisting of rigid plastic.

Micro particles are commonly used as a solid phase for binding various biological components, such as nucleic acids, proteins, toxins, cell organelles, bacteria or cells. For example, specific antibodies, oligonucleotides, polypeptides and lectins can be immobilized on the surface of micro particles. For example, enzymes can be immobilized on the surface of micro particles, whereupon the treatment and further use of the enzymes is efficient. Most of the so called magnetic nanoparticles (<50 nm) are not suitable to be treated with regular permanent magnets or electrical magnets, but require the use of an especially strong magnetic gradient, as described in EP 0842704 (Miltenyi Biotec). Magnetic particles, such as micro particles that have a diameter of about 0.1 µm or more, can usually be treated with regular permanent or electrical magnets. The viscosity of the solution can also considerably hamper the picking of the particles. The particles to be picked may originally be suspended in the solution, where a substance is desired to be bound, or say cells on the surface of the micro particles. It is of particular importance to be able to use large initial volumes in applications, where components are desired to be isolated for analysis. For example, efficient enrichment of pathological bacteria from a large sample volume to a little one is critical, because it has an effect on the sensitivity and time needed for analysis of a direct assay. At present there is no way sufficient enough to perform enrichment from a large volume to a little volume by means of micro particles. It would be preferable that a performance as described above would be as simple and efficient as possible.

PRIOR ART

Micro particles treated by means of a magnet have been used since the 1970's. This technique became very popular in immunoassays, among others. The use of micro particles in immunoassays to separate the bound antigen-antibody complex from the free fraction provided a considerable advantage especially in the reaction rate. The main development concerning the exploitation of micro particles has over the past years occurred in the field of molecular biology, microbiology and cell biology.

In a classical method the magnetic particles present in the reaction solution, such as micro particles, are captured by means of an external magnet to a given spot on the inner surface of the tube. Thereafter an effort is made to carefully remove the solution around the micro particles. In a classical method liquids are actively handled and magnetic particles stay in the same vessel during the whole procedure.

In another approach a magnet is used to actively transfer micro particles. The magnet is put in a solution containing micro particles, whereupon the magnet attracts micro particles in the solution and they form a solid precipitate. Thereafter the magnet and the micro particles can be drawn out of the liquid. Magnet together with its particles can thereafter be soaked in a liquid in another test tube, wherein the micro particles can be released from the magnet. In this method the treating, pipetting and aspiration phases are minimized to the extreme.

U.S. Pat. No. 3,985,649 (Eddelman), U.S. Pat. No. 4,272,510 (Smith et al.), U.S. Pat. No. 4,649,116 (Daty et al.), U.S. Pat. No. 4,751,053 (Dodin et al.) and U.S. Pat. No. 5,567,326 (Ekenberg et al.) describe solutions, wherein magnetable material is in each of them collected directly from the solution with a magnet. It is also common for these publications that the magnets are not protected with separate plastic shields. These solutions also require washing of the tip of the magnet before treating the next sample to eliminate the risk of contamination and the carry-over effect of impurities.

WO Application 87/05536 (Schröder) describes the use of a permanent magnet, movable inside the plastic shield, for picking ferromagnetic material from a solution containing them. Ferromagnetic material gathers to the tip of the magnet unit, while the magnet is in its lower position. The publication describes the transfer of the thus collected ferromagnetic material to a solution in another vessel and the release of the material there off the tip. The release of the ferromagnetic material is described by means of the design of the plastic shield that prevents the material from moving while moving the magnet upwards.

U.S. Pat. No. 5,837,144 (Bienhaus et al.) describes a method for collecting micro particles by means of a magnet equipped with a particular plastic shield. This publication describes the binding of micro particles from a solution, which is conducted out of the vessel by various arrangements. By moving the magnet the micro particles can be made to become free from the surface of the protective shield.

U.S. Pat. No. 5,942,124 (Tuunanen), U.S. Pat. No. 6,020,211(Tuunanen), U.S. Pat. No. 6,040,192 (Tuunanen), U.S. Pat. No. 6,065,605 (Korpela et al.), U.S. Pat. No. 6,207,463 (Tuunanen) and US Patent Application 20010022948 (Tuunanen) also describe devices equipped with a plastic shield for collecting micro particles from a solution and transferring them to another solution. These publications primarily describe solutions, where the intention is to treat micro particles in very little volumes. U.S. Pat. No. 5,942,124 (Tuunanen) describes a device, by means of which micro particles can be enriched right to the tip of the magnet unit. U.S. Pat. No. 6,020,211 (Tuunanen) describes the use of the device presented in the previous publication for transferring micro particles collected together by means of a big, so called classical magnet to smaller vessels. U.S. Pat. No. 6,040,192 (Tuunanen) describes an automated method for using micro particles in specific assays and for handling small volumes. U.S. Pat. No. 6,065,605 (Korpela et al.) continues to further apply the solution described in U.S. Pat. No. 5,942,124 (Tuunanen) for handling fairly large volumes. Now a method, whereby micro particles have first been collected by means of a particular magnet unit containing a big magnet, is described. Thereafter the magnet unit described in U.S. Pat. No. 5,942,124 (Tuunanen) is used for transferring the pellet of micro particles further to smaller vessels. U.S. Pat. No. 6,207,463 (Tuunanen) also applies the previously described magnet unit, by means of which magnetic particles can be collected right to the tip of the device. US Patent Application 20010022948 (Tuunanen) describes also the treating of a very small amount of micro particles in particular vessels designed for this purpose.

U.S. Pat. No. 6,403,038 (Heermann) describes a device that has a plastic shield and a permanent magnet attached to a particular bar. Micro particles are collected to the tip of the plastic shield and the method is intended in particular for to treat small volumes. The bas has a particular, projecting part, by means of which the magnet and the bar keep still in the protective tube.

EP 1058851 (Korpela) and Patent Application WO 01/60967 (Korpela) describe devices that have a stretchy, elastomer protective membrane. In these solutions the micro particles are collected on the surface of the stretchy protective membrane, whereupon they can be further transferred to another vessel. The protective shield of the magnet is made of stretchy material, whereby the membrane is as thin as possible when stretched. In this way a distance as small as possible from the magnet to the liquid is brought about.

Particularly U.S. Pat. No. 5,942,124 (Tuunanen), U.S. Pat. No. 6,020,211 (Tuunanen), U.S. Pat. No. 6,065,605 (Korpela et al.) and U.S. Pat. No. 6,207,463 (Tuunanen) and EP 0 787.296 (Tuunanen) describe a large amount of micro particles are intended for to be collected from a fairly large vessel by means of a very small magnet to the small tip of a very sharp and narrow bar, is impractical.

A large amount of micro particles can not be transferred to a small volume around a small spot, because the physical measures of the pellet formed by the micro particle mass grow quickly along with the liquid volume to be handled. A large micro particle mass has to be collected either over a large area or to a particular niche.

U.S. Pat. No. 4,738,773 (Muller-Rucholtz et al.), U.S. Pat. No. 5,972,721 (Bruno et al.) and U.S. Pat. No. 6,143,577 (Biscontee Sconte De Saint Julien; Jean Claude) describe treating micro particles in fairly large volumes by means of various flow-cell solutions. Also publication U.S. Pat. No. 6,159,689 (Adrian Parton) describes a method based on liquid flow and in this publication liquid is also being rotated in a tubing whereupon the efficiency of collecting micro particles is increased.

In practice, there are several limitations for the use of micro particles in large volumes to bind the desired biological components, such as viruses, bacteria, yeasts or parasites. The use of large amounts of micro particles, for example in routine assays for pathogenic bacteria, is impossible because of profitability reasons. It should be possible to use micro particles as little as possible, however in a sufficient amount, particularly in applications, where the presence or amount of biological components in a sample is desired to be determined. An additional prerequisite for the solution of this application area is that micro particles that have been used to pick the desired components out of the solution, should be carryable until the detection step. Large amount of micro particles can usually not be carried directly until the detection step, because the volumes used in the detection are often only 10-200 µl in their size.

The use of small amounts of micro particles is inefficient because of large solution volumes and problematic sample materials. The reaction rate i.e. time needed for the biological components to adhere to the surface of the micro particles decreases and collecting of micro particles gets considerably more difficult. Each time micro particles are bound with a magnet and released to a solution for the next collecting step some micro particles may be lost in the previous solution. This problem becomes particularly big in the case of large solution volumes and in the case where the sample contains a lot of particular material. Examples of such samples include food samples and bacterial homogenates.

None of the patents described above describe a method, whereby micro particles could be efficiently collected from very large liquid volumes and the collected micro particles released to a smaller liquid volume. The above-mentioned publications rather describe the handling of fairly small liquid volumes, such as 0.1-10 µl. If proteins, peptides, nucleic acids, cells, bacteria, viruses or other components are desired to be bound from a large volume on the surface of micro particles, there exists certain basic prerequisites for the optimal amount of particles to be used. Depending on the micro particles to be used, a preferable amount of particles per milliliter liquid to be isolated may be, for example, at least $10^7$ micro particles with a diameter of, for example, 1-5 µm. The amount of particles needed increases further, if a component, few in number, is desired to be bound as reliably as possible from a certain volume unit.

Neither does any of the above mentioned patent publications describe an efficient method for collecting the desired biological components (e.g. bacteria) from large volumes by using a relatively small amount of micro particles and enriching the collected micro particles and/or the biological component bound to the micro particles to a small volume.

MAGNETIC ENRICHMENT METHOD

This invention aims at bringing about such a method for isolating and enriching, for example, biological components or organisms in controlled conditions that does not have the disadvantages presented above. It is characteristic for a magnetic enrichment method according to the invention, that by means of the micro particles, attached to the magnet or attached by means of at least one magnet, at least one biological component is collected in a closed reactor vessel, and that at least one biological component is enriched in such a manner that the desired component is released to the solution.

The invention relates in particular to the use of micro particles in different reactor vessels, to their collection, enrichment and transfer from a solution to another. Binding of micro particles over a broad area on top of the protective shield brings about a large area and binding capacity that can be utilized while binding components from a great volume and releasing the bound components to a small volume. The method and equipment for treating also large amounts of magnetic particles in controlled conditions are described in the invention. The method can be used both with a manual and an automated device, where various transfers, washes and incubations of micro particles can be carried out. The possibility to rule and control the following conditions, among others, pH value and ionic strength of the solution, partial gas pressure and mixing of the solution in a particular reactor unit, is essential for the invention. It is possible to connect units that are intended for to detect, for example, PCR reactions and various labels, to the device.

Reactor Unit for Micro Particles

It is characteristic for a reactor unit for micro particles according to the invention that the reactor unit is a closed vessel, wherein the prevailing conditions are controllable. Reactor unit is a vessel or a reactor that can consist of various materials and have various shapes. The vessel forms a reactor chamber that may contain one or more holes for the in- and out-let of liquids. There can be an arrangement in the vessel that rotates the liquid being handled back inside the vessel. The vessel can be a part of a larger entity, where several different vessels of different sizes can be connected in an appropriate manner to each other. In a preferred embodiment of the invention the magnet unit according to the invention can also form a reactor unit.

Magnet Unit

It is characteristic for the magnet unit according to the invention that the shape and location of the magnet unit are adjusted in a preferable manner to collect the desired biological component.

In a preferred embodiment of the invention there is a ferromagnetic tube inside the magnet unit, by means of which the strength and the adjustment of the magnetic field can be regulated to the surrounding protective shield, around of which the micro particles are collected. The magnet can be moved in and out in relation to the ferromagnetic tube, whereupon the magnetic field of the magnet is changed. While the magnet is out, a magnetic field equal to the amount of magnet outside of the ferromagnetic tube is adjusted to the protective shield. Then micro particles can be collected outside of the protective shield. When the magnet is completely moved inside the ferromagnetic tube, there is no considerable magnetic field adjusting outwards. In this case the micro particles do not gather around the protective membrane, but stay in solution. The tube can be solid or adjustable in order to achieve the best possible efficiency for collecting.

Magnet unit can also consist of a magnet without a separate shield or protective membrane. The magnet can in this case be coated in an appropriate manner, for example, with an epoxy, phosphate or nickel coating.

In a preferred embodiment the magnet unit can be placed in a closed vessel or reactor, where liquid can be added when the need arises, and that may contain a valve to remove the handled liquid, thus, very large liquid volumes can be handled with the solution brought about. In another embodiment the magnet can have the shape of, for example, a bar, but it can also be of another kind. The magnet can be used as such, but in a third embodiment the magnet is coated with a protective coating or there is a protective layer around the magnet, such as, for example, a separate, hard protective shield or an elastic protective membrane.

If the reactor type described above is held on its side and the magnet unit can be rotated in relation to the protective shields of the reactor, thus, also mixing can be obtained with such a solution while treating liquid samples and micro particles. Micro particles can also be readily attached to the magnet unit or they can be attached in an appropriate manner during the process on top of the magnet unit and, thus, there will be a lot of active surface in the reactor. By mixing, the liquid to be handled may be made to flow between the micro particles in such a manner that the desired biological components, such as, for example, proteins, nucleic acids, viruses or bacteria attach to the micro particles on top of the magnet unit. Mixing can be organized by moving the magnet unit in relation to the surrounding vessel or vice versa. Mixing can also be organized by placing the whole reactor vessel in a particular mixer or shaker. On the other hand the liquid can be conducted between the micro particles by organizing the liquid flow in an appropriate manner inside the vessel or the reactor.

Mixing can also be mixing performed by means of the outer surface of the reactor, whereupon there may be appropriate projections or depressions inside the outer surface in order to bring about an efficient movement of the liquid inside the reactor vessel. In this case the magnet unit inside the reactor vessel is not moved. Mixing brough about with the magnet unit does not need to be rotational movement, but the mixing can be achieved by moving the magnet unit in an appropriate manner in the reactor vessel.

The magnet unit does not need to be fixed symmetrically in the reactor vessel, but it can be on one side of the reactor vessel or at an angle to the reactor vessel. The goal is to achieve by means of various ways of mixing an efficient mixing event and/or good efficiency for collecting micro particles.

The present device can be used for collecting micro particles from several different vessels or an arrangement may be made, where the liquid flow passes by the magnet unit. The latter case has the advantage that even large volumes can be operated in a relatively easy manner. Micro particles can be first free in the solution, from which they are then collected by means of the method according to the invention on top of the magnet unit. Micro particles can also be readily attached to the top of the magnet unit or the protective membrane of the magnet unit.

The length of the cylinder-shaped reactor vessel may vary. A very long tank may be preferable in some cases, where the greatest distance between the liquid and the magnet is desired to be kept as short as possible. Bags intended for homogenization, which bags are used in food diagnostics for the pretreatment of samples may also function as a reactor vessel according to the invention.

The reactor vessel can be such a vessel that has various structures inside of it, such as, for example, narrower areas, ailerons on walls, protuberances and mortises. These are intended for to bring about, for example, currents in the solution or to enhance the gathering of micro particles on the surface of the magnet unit. One possible shape of the reactor vessel is a sandglass-like structure, whereby the current can be focused in the narrowest spot of the vessel. The narrow spot can be appropriately extended and a magnet unit can be placed in this spot. Lifting and lowering the ends of the reactor can obtain vessel currents in the reactor vessel.

The reactor unit can also be a device, standing upright, with a flexible or a particular, depressible structure, such as a folding in the bottom. By using such a vessel an efficient mixing is brought about in the vessel.

A magnet unit according to an embodiment of the invention has the essential technical characteristic that the strength and the adjusting of the magnetic field can be regulated in relation to the protective membrane surrounding the magnet. This can be brought about by moving the magnet inside the ferromagnetic tube in such a manner that it can be completely inside the tube, whereupon the efficiency of the magnet is insignificant or nonexistent, or it can be partially or completely outside the tube, whereupon the efficiency and the collecting area of the magnet are in relation to the protruding part of the magnet. Combining these characteristics for transferring micro particles to vessels of appropriate sizes a very efficient collecting and enrichment event is brought about.

The equipment and the method described in the invention may be introduced when handling very large volumes and, on the other hand, it can also be applied for small volumes. The method is particularly efficient, when the magnet unit, the vessel to be used and the liquid volumes are mutually optimized. Particularly the use of the liquid volume displaced by the magnet unit for adjusting the height of the liquid surface is a very efficient way in the enrichment step for micro particles and biological components in the method. For the first time a device and a method, whereby the collecting area for micro particles and the strength as well as the physical location of the micro particles can be adjusted to the respective needs, is introduced.

The invention describes a method, whereby the magnet unit is taken away from the reactor unit and the micro particles gathered around the magnet unit are enriched in a small volume of solution. According to the invention, micro particles released to a small volume of solution can be further bound to the magnet unit and transferred to following vessels.

The way of enrichment according to the invention can also be used with a magnet without a shield, on top of which the micro particles are collected. The magnet can in this case be appropriately coated. The micro particles collected on top of the magnet do not in this case need to be released to a solution, but the biological components bound to the micro particles are released to a solution. The release of the biological components from the surface of the micro particles can be arranged either chemically (for example, by changing the pH value or the ionic strength of the solution or by means of particular reagents) or physically (for example, heating and ultra sound).

The invention describes ways to use small amounts of micro particles in large vessels and with problematic sample materials as well as to bring the magnetic particles directly to a small volume, for example, for further determination. The invention describes an efficient method for collecting micro particles from a large volume and also a way of binding the micro particles on the collecting surface, which is used for picking desired biological components from a solution.

By binding micro particles on an appropriate surface a very large collecting area is brought about. Micro particles bound to the surface can be coated, for example, with antibodies, by which the desired biological components are picked from the solution. An efficient way of collecting is brought about, when an area as large as possible is used for collecting micro particles over itself. Micro particles do not need to form a thick layer over the surface, but it is preferable to bring about a collecting surface as thin and vast as possible covered with micro particles. By means of a homogenous magnetic field the desired surface can be covered with micro particles by mixing the micro particles in the solution in an appropriate manner.

The surface of the protective membrane of a magnet unit or the surface of a magnet can be covered with micro particles in order to achieve an efficient collecting surface as described above. The covering can be made in a reactor vessel or other vessels, where a sufficient mixing of the micro particles is taken care of in order to achieve an even covering. The inner surface of the outer surface of the reactor unit can be covered with micro particles by means of magnets situated outside. In this way much more area for micro particle covering is obtained. The covering is done by moving the reactor vessel in an appropriate manner or by moving the micro particle solution inside the reactor vessel in another manner. Both the surface of the magnet unit and the inner surface of the outer surface of the reactor unit may in one case be simultaneously covered by micro particles. In this case magnetic fields outside the reactor vessel need to be removed at the stage, where the micro particles are desired to be collected around the magnet unit for further treatment.

Enrichment of micro particles and biological components described in the invention can be done in various ways, whereof the use of the dead volume in an appropriate vessel is one. In this way the magnet unit, where the micro particles are collected, is transferred to an appropriate vessel and the magnet unit displaces the solution in the vessel in such a manner that the surface of the solution rises along the magnet unit. By choosing the vessel, the volume of the solution and the magnet unit in an appropriate manner a situation is brought about, where the solution rises over the micro particles collected to the magnet unit. By removing the magnetic field from the magnet unit micro particles can be released to the solution. The magnetic field can be removed by moving the magnet quickly out of the inner side of the elastomer or non-elastomer shield of the magnet unit, by means of a ferromagnetic tube or by switching off the electrical magnet. By moving the vessel and the magnet unit thereafter up and down in relation to one another a good current is obtained in the solution and the release of micro particles from the surface of the protective membrane is enhanced. As a result the micro particles collected from a large volume or on the surface of the magnet unit are in a small volume of solution. By using a magnet without a shield in the magnet unit and micro particles gathered on the surface of the magnet, biological components bound to the micro particles can be released from the micro particles by utilizing the above mentioned, so called dead volume.

A preferable embodiment of this way of releasing is to use such a vessel that has a flexible or a particular depressible structure, such as, for example, a folding in the bottom. By using such a vessel a variation in the liquid surface in the vessel and an efficient current in releasing the micro particles is brought about. Carefully choosing the vessel to be used and the shapes of the magnet unit, efficient solutions suitable for handling a small volume of solution are found.

Another way to release the micro particles from the surface of the protective membrane of the magnet unit is to use such an oblong vessel, where the magnet unit is placed to rest lengthwise. In one embodiment the oblong vessel can be the reactor unit. The magnetic field is removed from the magnet unit in ways described above and the liquid inside the vessel touches with its whole length the protective membrane of the magnet unit. In this case the micro particles are released by rotating the magnet unit around its longitudinal axis in the solution inside the vessel. The moving promotes the release of micro particles to the solution. As a result the micro particles are released to a small amount of solution.

A ferromagnetic tube can consist of iron or other suitable material, which has appropriate characteristics to stop the magnetic stream from getting through the tube. The efficiency of the magnet can be regulated by changing the place of the magnet in relation to the ferromagnetic tube in such a manner that a part of the magnet is inside the tube. Alternatively the magnet can be kept still and the ferromagnetic tube is moved in relation to the magnet. The magnet is attached to a bar that can be ferromagnetic or is not ferromagnetic, and by means of which the magnet can be moved in the ferromagnetic tube.

The ferromagnetic tube described in the invention can be an individual tube, a set of several tubes together or an arrangement, where individual tubes make up a particular formation of tubes.

In particular when handling large volumes it may be preferable to incorporate several magnet units in a group of magnet units, whereby the collecting area for large masses of micro particles can be further increased. In addition, by designing the protective membrane preferable alternatives can be found for treating large masses of particles.

According to the invention there may be several magnet bars inside one protective membrane appropriately arranged by the inner circle of the protective membrane. This applies in particular to the case of a protective membrane of a very large size, whereby very large liquid volumes are handled. Another alternative is to use one very large magnet bar inside a protective membrane of large size.

According to a preferred embodiment of the invention the solution contains separate magnet units for collecting micro particles and a particular device or bar to move the liquid surface in an appropriate manner described in the invention. This solution enables approaches, whereby the magnet units do not move at all, but the moving of the liquid and the micro particles is performed by means of a unit particularly designed for this purpose. The vessel or reactor used in such a solution is appropriately designed to correspond to the described needs.

In an embodiment according to the invention there are several separate magnet bars, each of which includes an own protective membrane. These magnet bars can be grouped in an appropriate formation, such as, for example, fan-like in line, along the arc of a circle or several arcs of a circle within each other, whereby each bar gather an appropriate amount of particles around it.

In one case the ferromagnetic tube does not necessarily need to be used, when micro particles are desired to collect from a large volume and enriched in a small volume. In this case the magnet that is transversely magnetized is used, as described in the invention, and enrichment is carried out by utilizing the dead volume of the magnetic tool, respectively. In this case the magnet is quickly lifted upwards inside the protective membrane in such a manner that the micro particles do not follow. This option is also practicable when inside the protective membrane there is not space enough to use ferromagnetic tube. Examples for these cases are the very narrow vessels, where the micro particles are desired to release.

The magnet can have the shape of a round bar or a peg, but it can also have another shape. The magnetizing axis of the magnet may also vary. The magnetizing axis can be either longitudinal, whereupon it is parallel to the longitudinal axis of the bar and the poles of the magnet are at the ends of the bar. Then the magnetizing is parallel to the ferromagnetic tube, i.e. parallel to the direction of movement of the magnet or the tube.

However, the magnetizing axis of the magnet can also be transverse, whereupon it is perpendicular in relation to the longitudinal axis of both the ferromagnetic tube and the bar-like magnet. Then the direction of magnetization is transverse to the direction of movement of the magnet or the tube.

On the other hand the magnet can also consist of several separate magnets that can be alike or different and that can be attached to each other by means of magnetic force or through a material that is ferromagnetic or non-ferromagnetic. The magnet may also be a combination of magnetic and ferromagnetic material. The magnet may also be either a permanent magnet or an electrical magnet.

As one application the magnet may be composed of a magnet that is longitudinally and transversely magnetized. There may be ferromagnetic or non-ferromagnetic material between the magnets. In this special case there is a magnet placed at the end of the magnet unit, which magnet collects the micro particles very close to the tip i.e. the direction of magnetization is the same as the longitudinal axis of the magnet unit. This magnet is preferably a small-sized NdFeB magnet that may have a ratio between its diameter and its length of, for example, 1:1. This magnet solution is intended for to enhance the properties for enrichment and treatment of micro particles in small volumes. The protective membrane is in this case appropriately preformed or stretchy, and thereby applicable for treating micro particles in small volumes.

The invention presents that by designing the form of the outer surface of the plastic shield or the elastomer in a particular manner sufficient support is achieved to collect the mass of micro particles to be collected around the shield in a preferable and reliable manner. The term particular design of form refers to, for example, grooves, cavities and/or protuberances of different sizes and depths. When gathering between these formations, the pellet of micro particles gets particular support from the shield, while the magnet unit is moved against liquid currents. The effect produced by viscose samples is very significant, which means at worst that micro particles do not stay attached to a side of the shield, but stay in solution. The above-described form design has naturally a great benefit to the collecting reliability, when handling large volumes.

The protective membrane may consist of inelastic material, such as, for example, polypropylene, polystyrene, polycarbonate, polysulfone and polyethylene. The protective membrane may also consist of non-ferromagnetic metal or ferromagnetic metal. The protective membrane may also consist of stretchy elastomer material, such as, for example, silicone rubber, fluoroelastomer, polychloroprene, polyurethane or chlorosulfonated polyethylene. The protective membrane may also be treated with particular agents and thereby altering the properties of the protective membrane. The protective membrane may thus be coated with, for example, teflon (PTFE, polytetrafluoroethylene). It is particularly important to be able to select the protective material and the possible additional treatment in such a manner that the result enables action according to the invention even with very strong or corrosive chemicals. The shape of the protective membrane may be that of a tube, of a plate or it can be irregularly designed. There are particularly many alternatives when using an elastomer protective membrane, because then the magnet inside and the ferromagnetic tube may also give a shape to the protective membrane.

A preferred alternative to the protective membrane is an even or plate-shaped protective membrane consisting of stretchy material. Such a protective membrane may be an individual stretchy membrane in a particular frame. The frame is intended for to facilitate the use of the protective membrane and to bring about properties suitable for stretching the membrane. The use of such a protective membrane, consisting of one plate, is a recommended alternative when consumption of material is desired to be avoided in the isolation and washing events. The use of a protective membrane that has the shape of a plate is also economically more advantageous than the use of protective membranes of large size that have been prepared and designed with moulding tools.

The protective membrane may indeed be designed in such a manner that the micro particles stay attached as well as possible to the protective membrane while moving the transfer device despite of the emerging currents and despite of the penetration of the liquid surface and the effect of the surface tension on the liquid surface. Therefore various niches and protuberances can be made to the protective membrane, whereby a reliable transfer of the collected micro particles to another solution is brought about. Then the protective membrane may consist either of stretchy or inelastic material.

The protective membrane made of stretchy material may have a particular design that assures the reliable collection and transfer of a large amount of micro particles from a vessel to another. For this purpose the edges of the protective membrane may have particular protuberances and niches, where the micro particles gather. Then it is preferable to use a transversely magnetized magnet by means of which micro particles can be collected over a broad area. By designing the protective membrane particular structures supporting micro particle masses are brought about. The design also influences the disturbing effects of liquid currents and liquid tension. When using stretchy material and spots of varying thickness, the protuberances and niches of the protective membrane are stretched in various ways. This phenomenon can be efficiently utilized both in releasing micro particles and especially in bringing about an efficient mixing in the solution.

The micro particles may contain affinity ligands, enzymes, antibodies, bacteria, cells or cell organelles. Binding of the desired components can also be brought about by choosing the surface properties of the micro particles to be used and the composition of the buffers in an appropriate, preferable manner in order to bind the desired components from the samples. Examples include ion exchange, hydrofobic and reverse phase chromatography. Then, for example, binding and releasing of proteins from the surface of the micro particles is performed by means of appropriately chosen buffers and solutions. For example, salt content and pH value are then very important factors.

An affinity ligand may be, for example, a one- or two-stranded nucleotide sequence, such as, for example, DNA (Deoxyribonucleic Acid), RNA, mRNA or cDNA (Complementary DNA) or PNA (Peptide Nucleic Acid), a protein, a peptide, a polysaccharide, an oligosaccharide, a small molecular compound or a lectin. An affinity ligand may also be one of the following: Ovomucoid, Protein A, Aminophenyl Boronic Acid, Procion Red, Phosphoryl Ethanolamine, Protein G, Phenyl Alanine, Proteamine, Pepstatin, Dextran sulfate, EDTA (Ethylenediaminetetraacetic Acid), PEG (Polyethylene Glycol), N-acetyl-glucosamine, Gelatin, Glutathione, Heparin, Iminodiacetic Acid, NTA (Nitrilotriketic Acid), Lentil Lectin, Lysine, NAD (Nicotinamide Adenine Dinucleotide), Aminobenzamidine, Acriflavine, AMP, Aprotinin, Avidin, Straptavidin, Bovine Serum Albumin (BSA), Biotin, Concanavalin A (ConA) and Cibacron Blue.

Immobilizing an enzyme or an affinity ligand means that an enzyme or an affinity ligand is attached to the surface of the particles or that it is captured inside a "cage-like" particle, however in such a manner that the surrounding solution gets in contact with it.

Attaching the enzyme or the affinity ligand to the micro particles can be done by means of a covalent binding, for example, by means of the amino and hydroxyl groups in the carrier. Alternatively the binding can be brought about by means of a bioaffinity pair, for example, a biotin/streptavidin pair. According to one way the enzyme to be immobilized is produced with DNA technology, for example, in *Escherichia coli* bacteria and a particular enzymatic tail has been prepared to the enzyme. This affinity tail binds to micro particles, to which a strongly to the affinity tail in question binding component is attached in an appropriate manner. The affinity tail may be a small molecular compound or a protein. With this arrangement micro particles could be efficiently utilized while purifying the desired enzyme and, at the same time, the enzyme bound to the micro particles would be readily immobilized on the surface of micro particles to be used in the method described in the invention.

Attaching of the enzyme or the affinity ligand may also be unspecific, non-covalent, such as adsorption.

The tools and the method according to the invention enable the following solutions and properties:
1. The use of micro particles in controlled conditions by utilizing a particular reactor vessel.
2. Efficient enrichment of micro particles.
3. Collecting micro particles solely to one end of the magnetic tool or over the whole surface of the magnet.
4. Collecting micro particles from a large liquid volume.
5. Collecting a large amount of micro particles.
6. Preparing a collecting surface brought about with a small amount of micro particles.
7. Collecting micro particles while using a stiff plastic shield.
8. Collecting micro particles while using a stretchy, elastomer plastic shield.
9. Collecting micro particles without a particular shield.
10. The use of various vessels in enrichment.
11. Utilizing the displaced solution brought about by means of the magnet tool in the enrichment of micro particles.
12. Transferring micro particles through collecting and washing steps to the detection step.
13. The use of various magnets in order to bring about an optimal collecting geometry of micro particles.
14. Efficient mixing in the reactor vessel and in the enrichment vessel for micro particles.

By means of the invention a solution is found, which is optimal for broad use in collecting and transferring micro particles from both large and small liquid volumes. In particular, the invention promotes the collecting of particles in large liquid volumes and their release in small liquid volumes.

The device and the method according to the invention are not limited to, for example, molecular biology or purification of proteins, but they are generally applicable in fields, where ligands bound to micro particles can be used to synthetize, bind, isolate, purify or enrich biological components from various samples: diagnostic applications, biomedicine, enrichment of pathogens, synthesis of chemicals, isolation of poisons, viruses, bacteria, yeasts and cells.

Method Applications of the Invention

The device and the method according to the invention are applicable to be used in very many application areas, for example, protein chemistry, molecular biology, microbiology, cell biology and proteomics. The invention has applications in the industry, diagnostics, analytics and research.

For purifying proteins there is a need for purification experiments in small volumes and, on the other hand, to increase the capacity to even very large volumes. By means of the described invention protein purifications may be done, when the need arises, from various sample volumes. Protein chemists need to be able to purify protein from a sample that has been pre-treated as little as possible, such as, for example, cell lysates. It is also important to change the capacity of purification according to ever changing needs. At present it is possible by changing the column sizes to be used. As the purification proceeds, enrichment of the protein is one of the essential operations. In practice this means decreasing the liquid volume without any significant loss or denaturation of proteins. At present the most widely used methods include dialysis or filtration. Both of these methods require a lot of time. By means of the device and the method described in this invention a versatile method that is applicable for varying sample volumes, can be provided to the field of proteins. Changing the capacity is easy without buying or preparing new columns. For a larger sample volume a larger amount of micro particles is simply chosen and after the protein has been bound, micro particles and protein are collected out of the solution by means of the device and the method described in the invention. The washing steps can be performed either in the same vessel or by changing the vessel. In the previous case the washing buffers used need to be conducted out of the vessel and replaced with a fresh washing buffer. Changing the buffer may also be done by means of various valve or suction arrangements. After the washes the proteins bound to the micro particles may be released to a small volume and the protein solution may be efficiently enriched.

When the need arises, decreasing the volume can be performed in stages towards a smaller volume.

By means of the device and the method described in the invention, for example, ion exchange chromatography, reverse phase chromatography, hydrofobic chromatography and affinity chromatographic purifications can be made. Also gel filtration can be accomplished with the described device, but it requires performing the gel filtration in a column and thereafter collecting the micro particles by means of a device according to the invention and outflow of the proteins to a small volume. The method enables, for example, removing salt from samples without largely increasing the volume compared to classical gel filtration columns.

The use of immobilized enzymes to process various proteins, sugars, fats and various so called biopolymers is a very important application area for the described invention. An important characteristic compared to the use of soluble enzymes is the possibility to easily reuse the immobilized enzymes. Washing the immobilized enzyme by means of the described invention for further use is very easy and efficient.

Examples for essential groups of enzymes and individual enzymes, used for example in the industry, include:

CARBOHYDRASES: Alpha-Amylases, Beta-Amylase, Cellulase, Dextranase, Alpha-Glucosidase, Alpha-Galactosidase, Glucoamylase, Hemicellulase, Pentosanase, Xylanase, Invertase, Lactase, Pectinase, Pullulanase PROTEASES: Acid Protease, Alkaline Protease, Bromelain, Ficin, Neutral Proteases, Papain, Pepsin, Peptidases, Rennin, Chymosin, Subtilisin, Thermolysin, Trypsin LIPASES AND ESTERASES: Triglyceridases, Phospholipases, Esterases, Acetylcholinesterase, Phosphatases, Phytase, Amidases, Aminoacylase, Glutaminase, Lysozyme, Penicillin Acylase ISOMERASES: Glucose Isomerase, epimerases, racemases OXIDOREDUCTASES: Amino Acid Oxidase, Catalase, Chloroperoxidase, Glucose Oxidase, Hydroxysteroid Dehydrogenase, Alcohol dehydrogenase, Aldehyde dehydrogenase, Peroxidases LYASES: Acetolactate Decarboxylase, Aspartic Beta-Decarboxylase, Fumarase, Histidase, DOPA decarboxylase TRANSFERASES: Cyclodextrin Glycosyltranferase, Methyltransferase, Transaminase, Kinases

LIGASES

PHOSPHATASES: Alkaline Phosphatase

The use of enzymes is very common in many branches of the industry, some examples of which follow: the synthesis and modification of lipids, proteins, peptides, steroids, sugars, amino acids, medicines, plastics, fragrances, chemicals and so called chiral chemicals.

Various synthesizing and cleaving enzymes associated to glycobiology, such as, for example, endo- and exoglycosidases, are also within the scope of the invention. Enzymes familiar from applications of molecular biology, such as restriction enzymes, nucleases, ribozymes, polymerases, ligases, reverse transcriptases, kinases and phosphatases are also within the scope of the method described in the invention. As examples of DNA/RNA modifying enzymes the following can be mentioned: CIAP (Calf Intestinal Alkaline Phosphatase), *E. Coli* alkaline phosphatase, exonucleases (for example, P1 nuclease, S1 nuclease), ribonucleases, RNases (e.g. Pancreatic RNase, RNase H, RNase T1, RNase M, RNase T2), DNA ligases, RNA ligases, DNA polymerases, Klenow enzyme, RNA polymerases, DNA kinases, RNA kinases, terminal transferases, AMV reverse transcriptase and phosphodiesterases. The use of these and other DNA/RNA modifying enzymes is very polymorphous both in the research and applications of molecular biology. Proteases are very important enzymes in proteomics and protein chemistry, example of which include trypsine, chymotrypsine, papain, pepsin, collagenase, dipeptidyl peptidase IV and various endoproteinases. Synthetic enzymes, catalytic antibodies and multi-enzyme complexes may be used in the ways described in the invention. The use of the invention is neither limited by the use of enzymes and other catalytic components in waterfree conditions, for example in organic solvents.

Biocatalysis commonly refers to the use of bacteria, enzymes or other components containing enzymes in the process. Enzymes or bacteria can be immobilized to a suitable solid carrier and the agent being treated is brought into connection with the immobilized components by using, for example, classical columns. According to this invention cells or enzymes can be attached to micro particles in an appropriate manner, which micro particles may then be used according to the invention to perform various enzymatic reactions.

The method described for culturing and isolating cells may be broadly utilized. Cells of interest include, for example, stem cells, B lymphocytes, T lymphocytes, endothelial cells, granulocytes, Langerhans cells, leucocytes, monocytes, macrofages, myeloid cells, natural killer cells, reticulocytes, trophoblasts, cancer cells, transfected cells and hybridoma cells. Commonly known methods, such as, for example, a direct or indirect isolation method, may be used in isolation of cells. In the first one, the direct isolation method, the desired cells are separated by binding them to the surface of micro particles by utilizing, for example, specific antibodies. In the indirect method, not the desired cells, but all the other cells are bound to the micro particles. The desired cells stay in this case in the solution.

The method described in the invention applies well to the culture, isolation, purification and/or enrichment of bacteria, viruses, yeasts and many other uni- or multicellular organisms. A particularly important application area is the enrichment of pathogenic bacteria, such as, for example, *Salmonella, Listeria, Campylobacter, E. Coli* 0157 and *Clostridium*, viruses, parasites, protozoans or other small organisms from a large liquid volume. The device and the method described in the invention can be exploited also within these application areas.

Isolation of cell organelles and various cell fractions is also within the scope of the application area of the invention. Cell organelles may be purified in a normal manner by utilizing, for example, specific antibodies and various affinity ligands.

There are different needs to purify nucleic acids, starting from the purification of tiny amounts of DNA (Deoxyribonucleic Acid), RNA (Ribonucleic Acid) or mRNA (Messenger RNA) until large volumes of several liters. The method according to the invention can be used to isolate nucleic acids from both large and small sample volumes efficiently.

By means of the method a chain can be formed between culturing/growing, isolation and purification events according to various needs. The desired cells may, for example, first be cultured in appropriate conditions and be enriched after culturing. Thereafter, for example, the cell organelles can be isolated from the cells. The cell organelles are purified and the process may continue, for example, with purification of DNA or proteins. Micro particles equipped with various coatings and characteristics can be used in stages during the process. The last stage may be for example, enrichment of the purified product to the desired volume, amplification and detection of the product.

BRIEF DESCRIPTION OF THE DRAWINGS

FIG. 14a presents a magnet unit placed in a mixing vessel equipped with a flexible element.

FIG. 14b corresponds to FIG. 14a and presents the mixing vessel equipped with an flexible element in another position.

FIG. 15a-c present vertically sectioned side views of the various stages when using the magnet unit together with a tube consisting of stretchy material.

FIG. 16a-f present vertically sectioned side views of the various stages for treating the solution in the tube by means of a magnet unit.

DETAILED DESCRIPTION OF THE DRAWINGS

Figure 1:
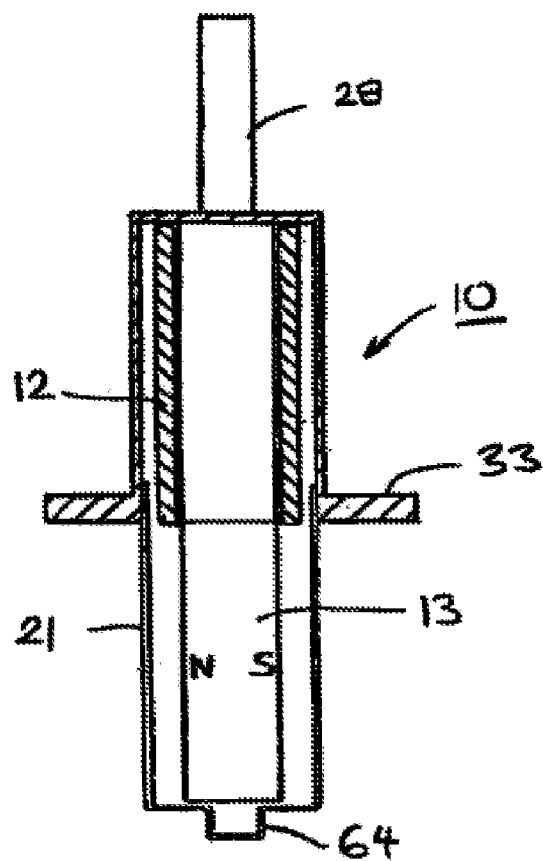
FIG. 1 presents a partially sectioned side view of an embodiment of the magnet unit.

FIG. 1 presents a magnet unit 10 according to the invention, which magnet contains a transversely magnetized magnet 13 and a ferrometallic tube or sleeve 12, which is transferable in axial direction on top of the magnet 13. The magnet 13 is protected by a protective membrane 21, which may consist of stretchy or hard material, preferably plastic or silicone rubber. In addition a flange joint 33 and a rotation axis 28 are included in the magnet unit 10, by means of which the rotation axis of the magnet 13 and the protective membrane 21 inside the magnet unit 10 may be rotated around their longitudinal axes.

Figure 2:
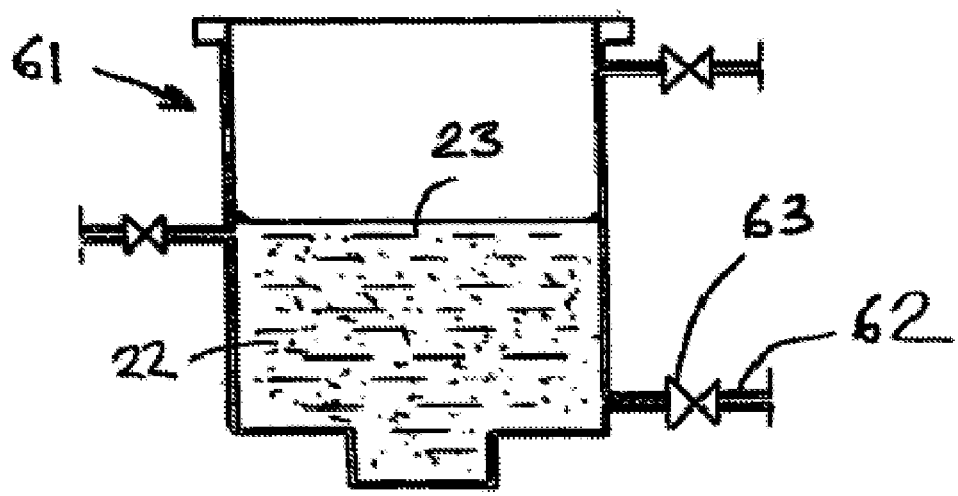
FIG. 2 presents a sectioned side view of a reactor vessel according to the invention.

FIG. 2 presents a reactor vessel 61 according to the invention, which contains channels 62 equipped with valves 63. The reactor vessel 61 contains liquid 23 needed in the process. The reactor vessel 61 and the magnet unit 10 presented in FIG. 13 together form a reactor unit 60, as described in FIG. 15.

Figure 3:
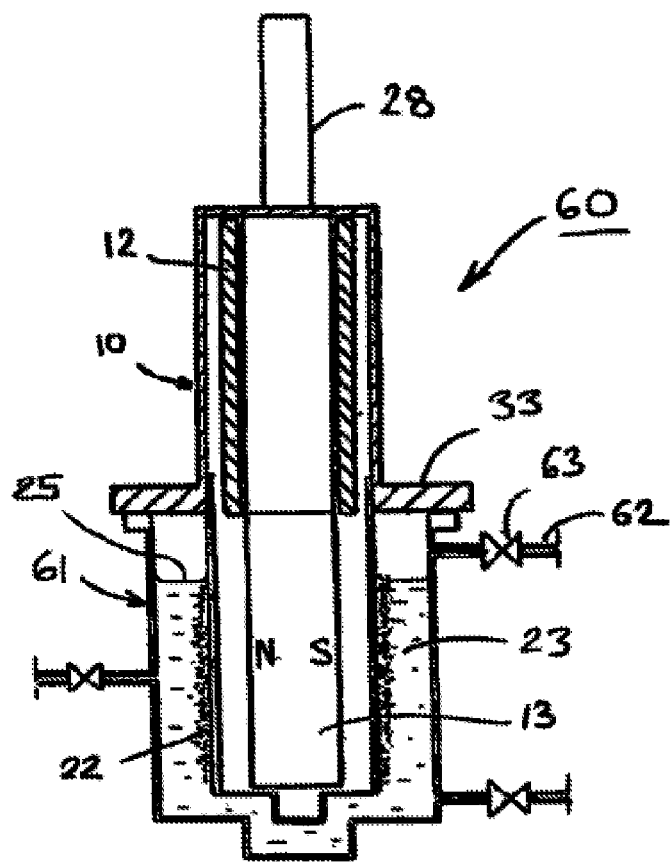
FIG. 3 presents a partially sectioned side view of a reactor unit according to the invention.

FIG. 3 presents a reactor unit 60 according to the invention, which reactor unit contains a reactor vessel 61 containing liquid 23 needed in the process, which includes, for example, culture media, sample, buffer solution and magnetic particles 22, such as micro particles. Agents, such as appropriate solutions and magnetic particles, may be added to the reactor 60 when the need arises or liquids may be removed through channels 62 connected to reactor vessel, which channels contain valves 63. The channels 62 or corresponding inlets may be located on the sides or at the ends of the reactor vessel and there may be several of them in various parts of the reactor unit. By means of channels 62, for example, gases, pH value and salt content inside the reactor unit 60 can be controlled. Through the inlet channel 62 also more sample may be brought to the reactor unit 60 and/or sample that has been inside the reactor unit 60, may be removed. These inlets may have appropriate filters, by means of which the gas or solution taken inside may be kept sterile. Magnetic particles 22 have been gathered on the surface of the protective membrane 21 in FIG. 15.

Figure 4:
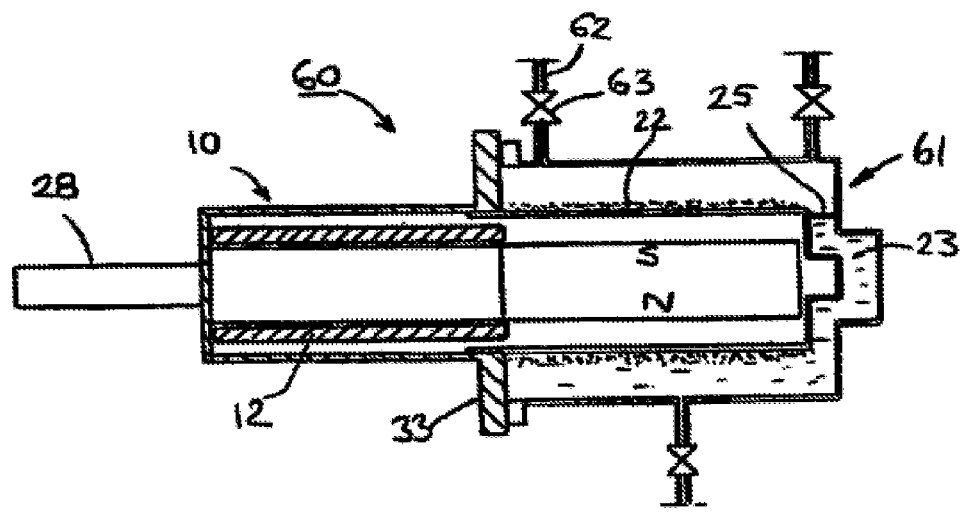
FIG. 4 presents the reactor unit of FIG. 3 in a horizontal position.

FIG. 4 presents the reactor unit 60 of FIG. 3 in a horizontal position. If the reactor unit 60 is kept on its side in this position and the magnet 13 and the protective membrane 21 of the magnet unit 10 are rotated in relation to the protective shield of the magnet unit 10, an efficient mixing is brought about in liquid 23 inside the reactor unit 60. Then also magnetic particles are mixed in the liquid. The height of liquid surface 25 inside the reactor unit 60 may be regulated and optimized according to the application used.

In order to increase the efficiency of mixing liquid 23 inside the reactor unit 60, the protective membrane 21 of the magnet 13 may be equipped with appropriate ailerons. While the protective membrane 21 and the ailerons rotate, moving and mixing of liquid 23 inside the reactor vessel 63 is achieved. Instead of ailerons the surface of the protective membrane 21 may be designed in various ways. The protective membrane 21 may also have an appropriate design in its tip 64, which thereby supports the magnet unit, while it is horizontally on its side.

In the process to be used the magnetic particles may be readily attached to the protective shield 21 of the magnet 13 or they may be attached to it in an appropriate manner during the process. Collecting and releasing of magnetic particles from the protective membrane 21 is according to the invention brought about by means of a ferromagnetic sleeve 12, which is transferred longitudinally on top of or off the magnet 13. the magnet 13, used in the presented embodiment, is a longitudinally magnetized magnet. Then it is essential that magnetic particles may be collected in the reactor unit 60 over a large area surrounding the protective membrane 21.

While the magnetic particles are attached to the protective membrane 21, the tool has very much active surface for collecting, for example, proteins, cells, DNA or bacteria from liquid 23 in the reactor vessel 61. By mixing the solution the solution to be treated is made to flow between the magnetic particles attached to the protective membrane 21 in such a manner that the desired components bind to the magnetic particles. It is also possible in the reactor unit 60 to release the magnetic particles now and then to the solution in the way described in the invention and to pick the magnetic particles again from the solution on the surface of the protective membrane 21.

Figure 5:
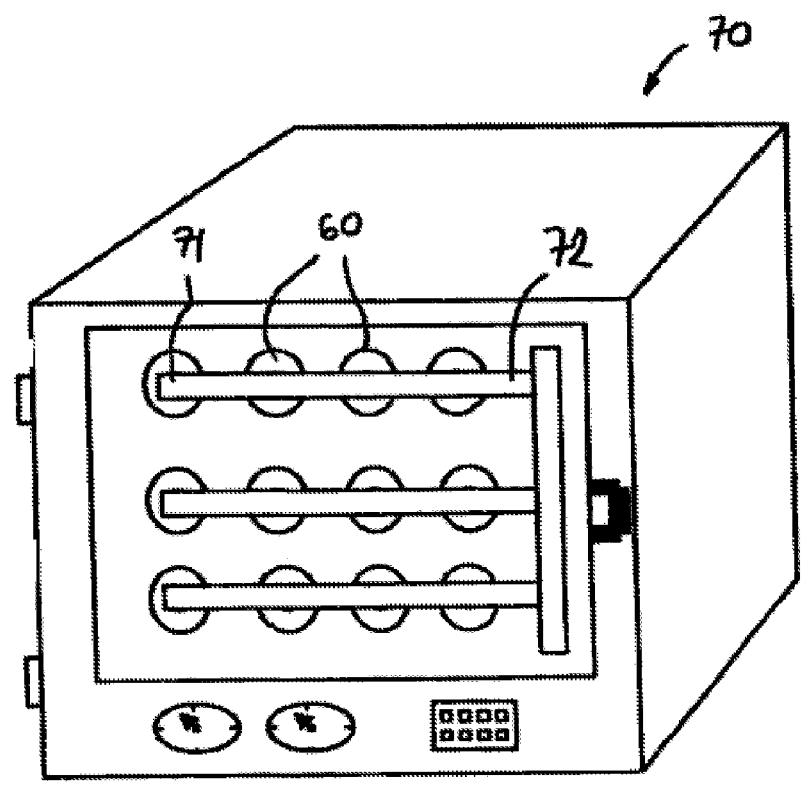
FIG. 5 presents a perspective view of an environmental cabinet according to the invention.

FIG. 5 presents an environmental cabinet 70, where several reactor units can be placed simultaneously. By means of a motor 71 and a drive mechanism 72 connected to the environmental cabinet 70, magnets 13 and protective membranes 21 inside the reactor units 60 may be rotated simultaneously. For example, temperature, rotation speed of the magnets and the protective shields, gas exchange between the reactor units, sampling of the reactor unit and additions of sample or solutions to the reactor units may be regulated in the environmental cabinet 70.

Such a solution is particularly useful in microbiological quality control, whereby, for example, pathogenic bacteria may be cultured in the reactor units 60. In an appropriate time the reactor units 60 are taken away from the environmental cabinet 70. Then the micro particles are gathered on the surface of the protective membrane 21 in the magnet unit 10. The magnet unit 10 of the reactor 60 is released from the reactor vessel 61, whereupon the magnetic particles may be, for example, washed and enriched in separate vessels. Everything else but the magnetic particles will stay in the released reactor vessel 61. Very large volumes may be handled with the equipment.

Figure 6:
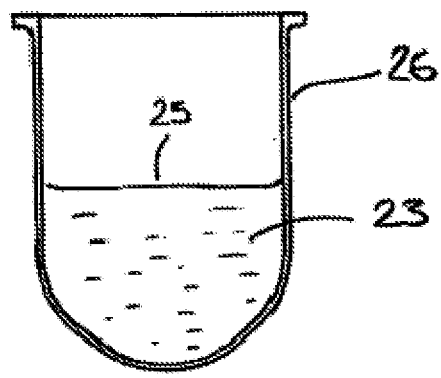
FIG. 6 presents a sectioned side view of a tube.
Figure 7:
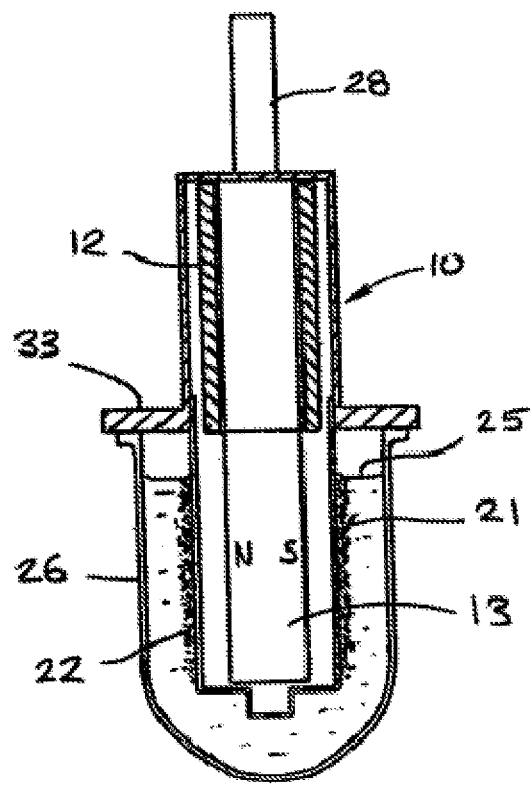
FIG. 7 presents a sectioned side view of a magnet unit connected with the tube, the sleeve of the magnet unit being in the first position.

FIG. 6 presents a tube 26, which contains appropriate liquid 23, such as washing fluid. The magnet unit 10 released from the reactor 60 is brought to tube 26 in the way presented in FIG. 7. Magnetic particles 22 are at this point still gathered on the surface of the protective membrane 21. In this situation the liquid surface 25 of the solution 23 has to be above the binding area of the magnetic particles 22 on the surface of the protective membrane 21 in such a manner that the magnetic particles 22 are below the liquid surface 25.

Figure 8:
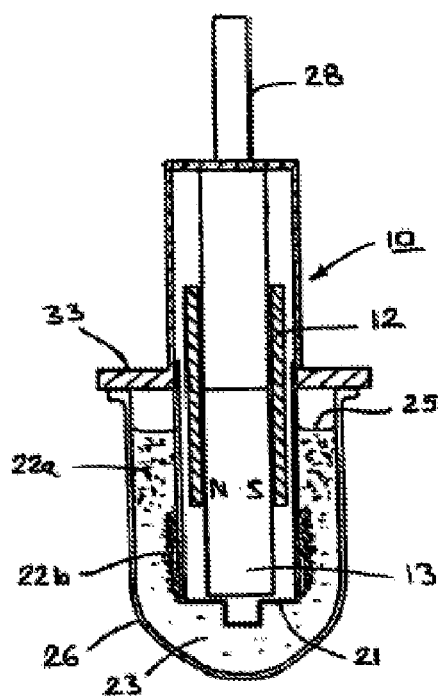
FIG. 8 corresponds to FIG. 7 and illustrates a situation, where the sleeve of the magnet unit is in the second position.

FIG. 8 presents a situation, where the ferromagnetic sleeve 12 of the magnet unit 10 is moved downwards in the figure. It is seen in FIG. 8 that the ferromagnetic sleeve 12 is already partially on top of the magnet 13. The transfer of the ferromagnetic sleeve 12 on top of the magnet 13 brings about the removal of the magnetic field in that spot, whereupon a part of the magnetic particles 22a are released from the surface of the protective membrane 21 from above. In the spot, where ferromagnetic sleeve 12 is not yet on top of the magnet 13, the magnetic field still keeps the other part of the magnetic particles 22b attached on the surface of the protective membrane 21.

Figure 9:
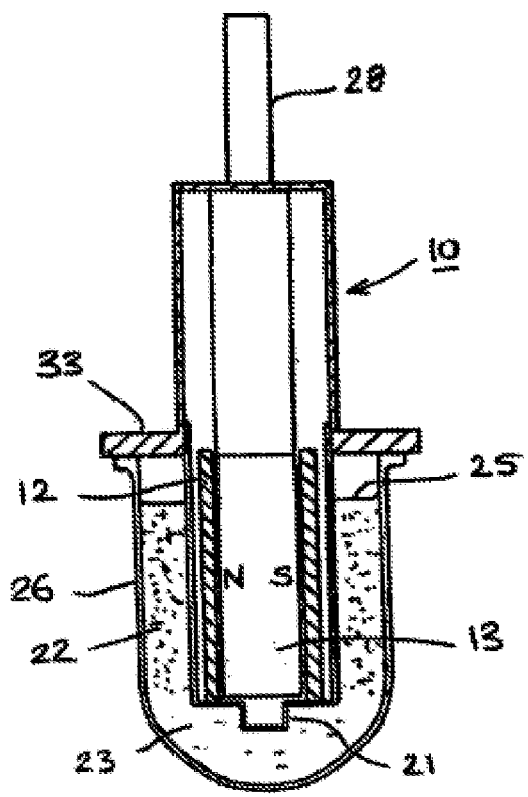
FIG. 9 corresponds to FIG. 7 and illustrates a situation, where the sleeve of the magnet unit is in the third position.

In FIG. 9 the ferromagnetic sleeve 12 is completely transferred on top of the magnet 13. Then the ferromagnetic sleeve 12 has brought about a complete removal of the magnetic field, whereupon the magnetic particles 22 are released from the surface of the protective membrane 21 to solution 23.

Figure 10:
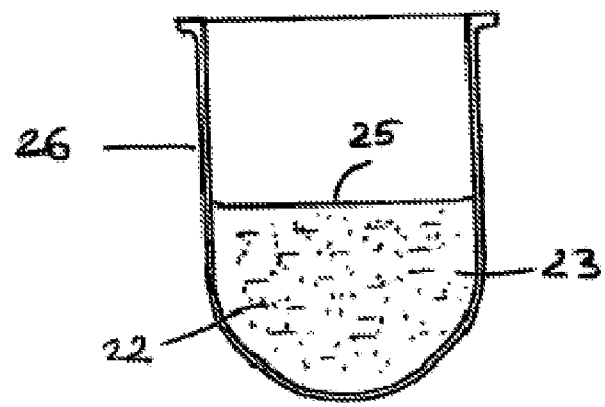
FIG. 10 corresponds to FIG. 6 and presents the tube in another situation.

In FIG. 10 the magnet unit 10 is removed from the tube 26, whereupon enrichment of the magnetic particles 22 and components bound to these, such as, for example bacteria, is achieved in the tube 26 outside the reactor unit 60. By using the same magnet unit 10, processing of the sample may now be continued in smaller volumes in such a manner that the collecting area of the magnetic particles 22 is limited by means of the ferromagnetic sleeve 12 right to the tip of the protective membrane 21. The magnetic particles 22 may be collected from the tube 26 to following tubes and, for example, washed in a sufficient amount.

It is also possible to isolate DNA, RNA, protein or surface antigen of bacteria from the reactor unit 60 by means of reagents intended for this. Bacteria usually needs to be broken by means of various devices and/or reagents before further analyses. Thereafter the following micro particles with various binding properties may be added to the bacterial lysate. By means of magnetic particles with a new characteristic, for example, the desired protein, antigen, DNA, rRNA, RNA or mRNA of bacteria may be collected from the bacterial lysate. The magnetic particles 22 intended for to collect bacteria in the reactor unit 60 may have been removed before magnetic particles with new characteristics have been introduced in the process.

The above mentioned components may be isolated, washed and released for the primary analysis with the method described in the invention. Analysis methods may include, for example, PCR amplification or an ELISA assay. In the described reactor vessel 61 aerobic and anaerobic microorganisms may be cultured. Culturing eukaryote cells is also possible by using the reactor vessel according to the invention.

Figure 11:
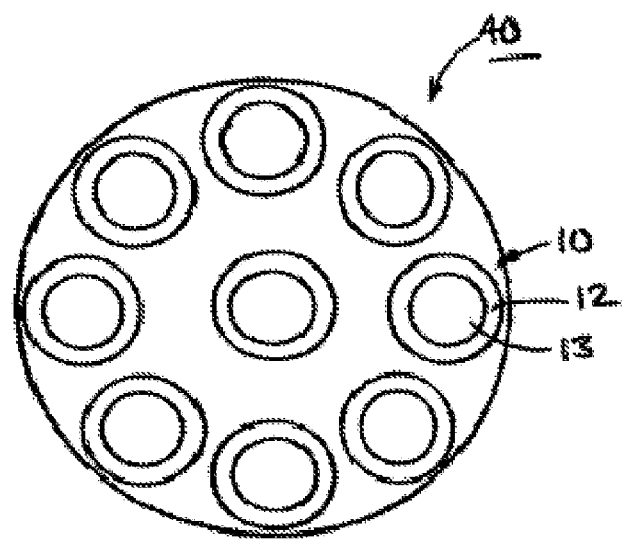
FIG. 11 presents a diagrammatic top view of parallel magnet units placed in a circular arrangement.

FIG. 11 presents a multi-channel transfer device 40, wherein the magnet units 10 form a circle. Each magnet unit 10 may have a separate protective membrane, but according to another embodiment there is one shared protective membrane for all the magnet units 10.

Figure 12:
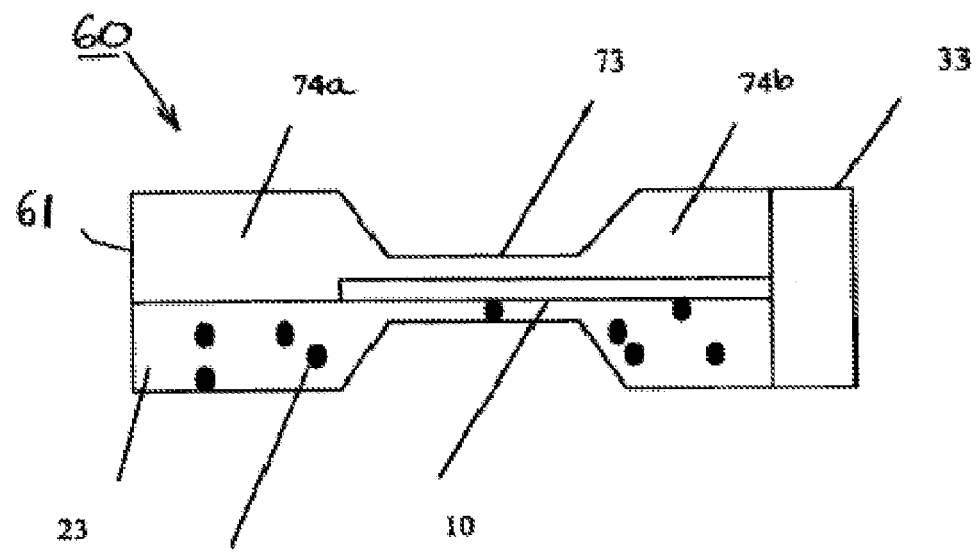
FIG. 12 presents a reactor unit according to the invention.

FIG. 12 presents a reactor unit 60 according to the invention, where liquid 23 needed for the process is placed to the reactor vessel 61. Liquid 23 may contain the liquid needed for the process, growth media, sample, buffer solution and micro particles 22. The reactor vessel 61 is connected and preferably also sealed to the flange joint 33 of the magnet unit 10. There is a narrowing 73 in the middle of the magnet unit 10 and the magnet unit 10 is focused in the same spot inside the reactor vessel 61. The narrowing 73 divides the inner space of the reactor vessel 61 longitudinally to two separate compartments 74a and 74b. By moving the reactor unit 60, for example, around its longitudinal axis, an efficient current around the magnet unit 10 is brought about in the reactor vessel 61 by the narrowing 73. The movement of the reactor unit 60 may be different, for example in such a manner that the reactor unit 60 is rocked around its transverse axis, whereupon the ends are by turns higher or lower than the opposite end.

Figure 13A:
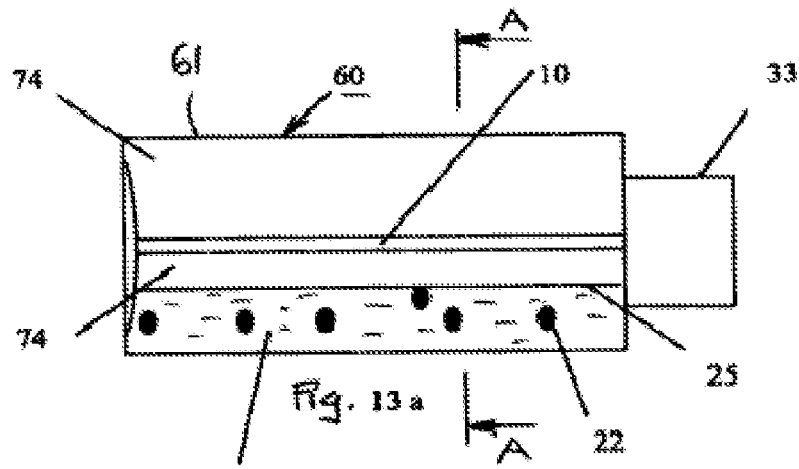
FIG. 13a presents a vertically sectioned side view of another reactor unit according to the invention.
Figure 13B:
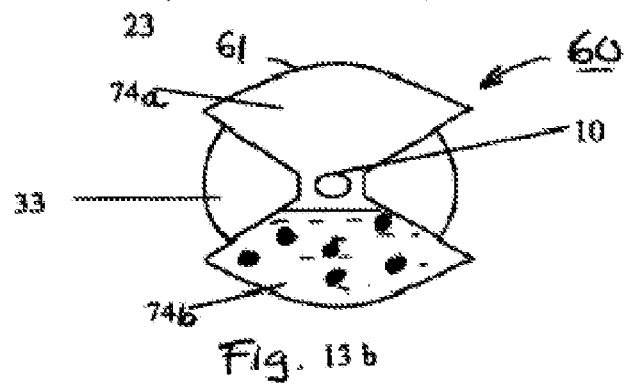
FIG. 13b presents a section taken from FIG. 13a along the line A-A.

FIGS. 13*a* and 13*b* present another reactor unit 60 according to the invention, where liquid 23 needed in the process is placed in the reactor vessel 61. Liquid 23 contains the solution needed in the process, such as culture media, sample, buffer solution and micro particles 22. The reactor vessel 61 is connected to a flange joint 33 of magnet unit 10, whereby a closed reactor vessel 60 is formed.

A horizontal cut of the reactor unit 60 presented in FIG. 13*b* shows that there is a narrowing 73 in the middle of the reactor unit 60 and the magnet unit 10 is focused in the same spot inside the reactor vessel 61. The narrowing 73 divides the inner space of the reactor vessel 61 transversely to two separate compartments 74*a* and 74*b* that are situated on top of each other in FIG. 13*b*. Liquid 23 is in FIG. 13*b* completely in the lower compartment 74*b*. When the reactor unit 60 is rotated around its longitudinal axis, the position of the compartments 74*a* and 74*b* changes in relation to each other. Then the compartments 74*a* and 74*b* are by turns above each other, whereby an efficient current around the magnet unit 10 by the narrowing 73 is brought about in the reactor vessel 61.

FIGS. 14*a* and 14*b* present a magnet unit 10 and another vessel, which may also act as a reactor unit 60 and/or a tube 26 according to the invention. In FIG. 14*a* the vessel contains a magnet unit 10 and liquid 23. In FIG. 14*a* the surface of the liquid 23 is at height h1. The vessel 26 contains a flexible element 75, which in FIG. 14*a* is in its basic position. In FIG. 14*b* the flexible element 75 is pushed downwards, whereupon the surface of the liquid 23 has arisen to height h2. By changing the length of the flexible element 75 the current and the surface of the liquid 23 in the vessel may be affected.

FIG. 15*a* presents a tube 26 consisting of stretchy material, which tube contains solution 23. In FIG. 15*b* the magnet unit 10 is brought to the vessel, which magnet unit has been used to push downwards the bottom of the tube 26 consisting of stretchy material. At the stretched stage the surface 25 of the solution 23 is made to rise in an efficient manner along the magnet unit 10. FIG. 15*c* presents a situation, where the magnet unit 10 has been removed from the tube 26 and the liquid surface 25 has come down again to the original level. Such a solution may be utilized in enrichment of micro particles according to the invention.

FIGS. 16*a*-*f* present a method according to the invention for enrichment of micro particles 22 to a small volume and to transfer the micro particles 22 to the following vessel in the tip of the magnet unit 10. There is a tube 26 in FIG. 16*a*, which tube contains solution 23. In FIG. 16*b* the magnet unit 10 that has micro particles 22 surrounding its protective membrane 21, is brought to the tube 26. The magnet unit 10 and an appropriately chosen tube 26 rise surface 25 of the solution 23 in an appropriate manner over the micro particles 22 collected by the magnet 13*a*. The magnet unit 10 contains a group of magnet units 41 that includes both a first magnet 13*a* magnetized transversely to its longitudinal axis and a small, second magnet 13*b* magnetized along its longitudinal axis right in the tip of the magnet unit 10, which is presented in the lower part of FIG. 16*b*. The small magnet 13*b* is intended for to act in the transfer of the micro particles 22 to small vessels at the next stages of the process.

FIG. 16*c* presents a situation, where a group of magnet units 41 is quickly moved out of the protective membrane 21. Then the micro particles do not move together with the magnets 13*a* and 13*b*, but stay in the spot, where they were before the quick movement of the magnets. FIG. 16*d* presents a situation, where the protective membrane 21 has been moved in the tube 26 and the micro particles 22 have been made to become free from the surface of the protective membrane 21 to the solution 23. FIG. 16*e* presents the use of the magnet unit 10 while collecting micro particles 22 in the tube 26 right to the tip of the magnet unit 10 by means of the small magnet 13*b*. In FIG. 16*f* all micro particles have been collected from the solution 23 and transferred by means of the magnet unit 10 to, for example, the following vessels that contain other appropriately chosen solutions.

Figure 17:
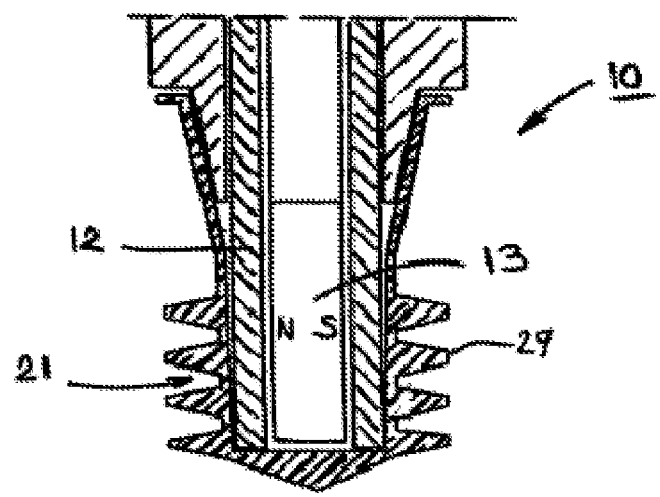
FIG. 17 presents a partially sectioned side view of an embodiment of the magnet unit equipped with a protective membrane.

FIG. 17 presents a magnet unit 10 that includes a transversely magnetized magnet 13, a ferromagnetic sleeve 12 and a protective membrane 21 that contains ridges 29 on its outer surface. Between the ridges 29 there are niches, where micro particles 22 gather and by means of which reliable collection of a large amount of micro particles to broad surfaces and their transfer from one vessel to another is assured.

Figure 18:
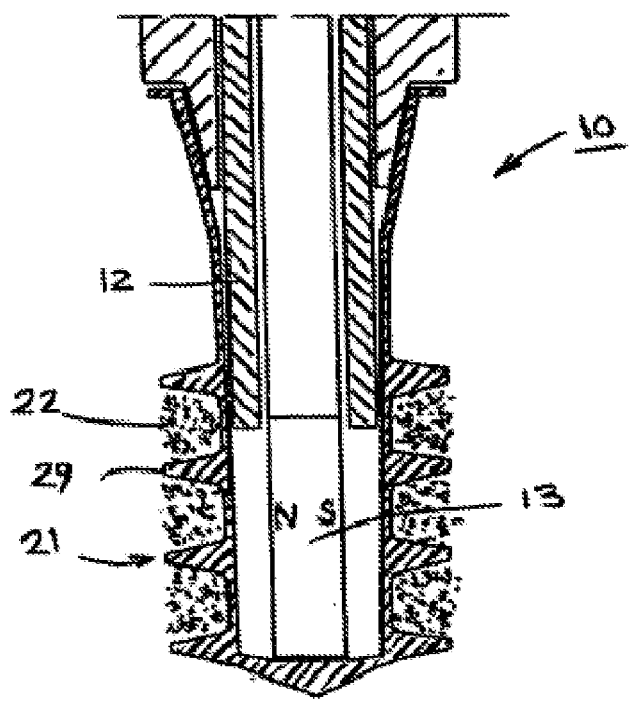
FIG. 18 corresponds to FIG. 17 and presents the action of the magnet unit in another stage.

FIG. 18 presents the magnet unit 10 of FIG. 17 in a position, where the magnet 13 is pushed completely out of the ferromagnetic sleeve 12. Then the transversely magnetized magnet 13 collects micro particles 22 to its protective membrane 21 with its whole length. When pushing the magnet 13 out, the protective membrane 21 thereby stretches in such as manner that large niches or pockets will form between ridges 29. The micro particles 22 will stay in these pockets in such a manner that it is easy to keep them still in place while lifting the magnet unit 10. The liquid currents caused by the movement of the magnet unit 10 and the disturbing effect of surface tension caused by penetration of the surface do not release micro particles 22 from the pockets.

Figure 19:
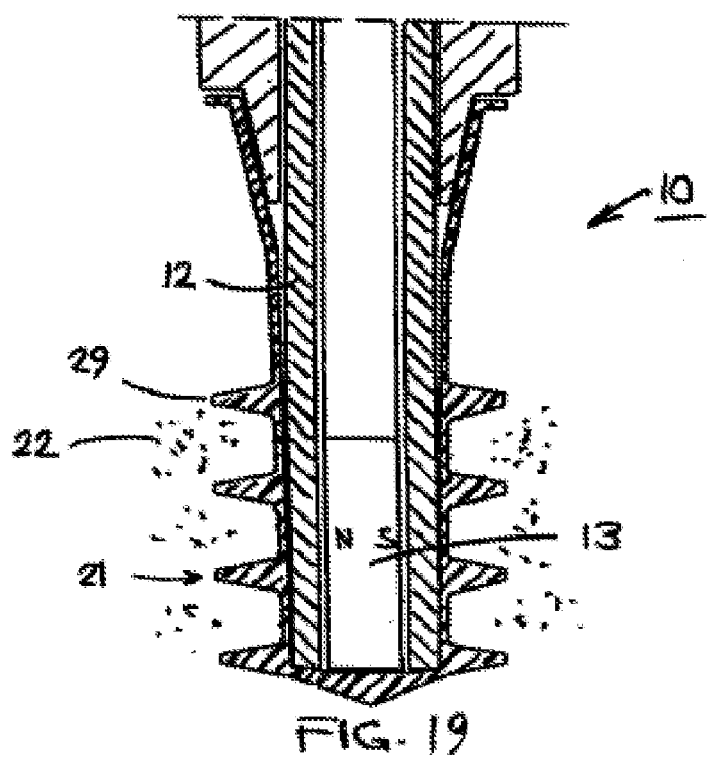
FIG. 19 corresponds to FIG. 17 and presents the action of the magnet unit in the third stage.

FIG. 19 presents a situation, where the magnet 13 is pushed completely out of the ferromagnetic sleeve 12 and simultaneously the ferromagnetic sleeve 12 is also pushed completely out. Then the ferromagnetic sleeve 12 pushed on top of the magnet 13 neutralizes the magnetic force of the magnet, 13 and the micro particles 22 are released from the protective membrane and transferred to the liquid.

Figure 20:
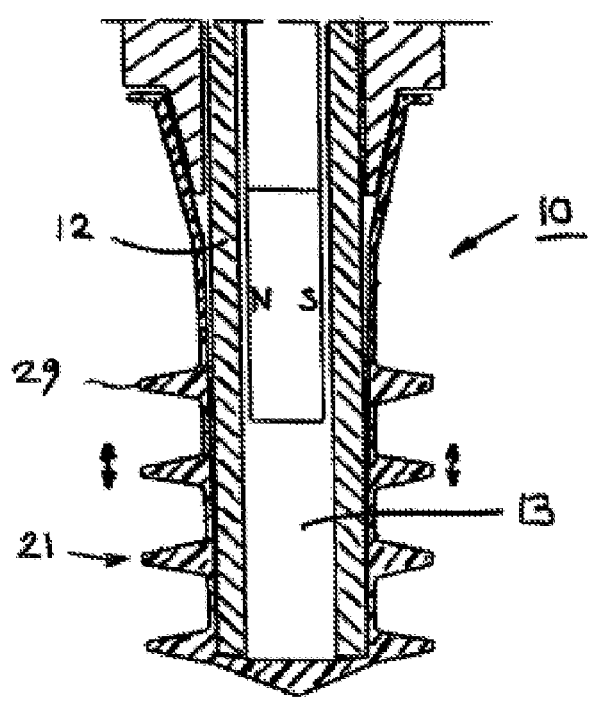
FIG. 20 corresponds to FIG. 17 and presents the action of the magnet unit in the fourth stage.

FIG. 20 again presents a situation, where only the ferromagnetic sleeve 12 is completely pushed out. In this case the magnet 13 does neither have magnetic force, and so the micro particles 22 do not gather on the surface of the protective membrane 21. This stage presented in FIG. 26 can instead be used by turns with the stage presented in FIG. 23, whereby an efficiently mixing pump effect is brought about in the liquid. Also the stages presented in FIGS. 18 and 19 can naturally be used by turns that is, while the magnet 13 is completely pushed out, only the ferromagnetic sleeve 12 is moved back and forth. A mixing pump effect is achieved also in this manner in the liquid.

Figure 21:
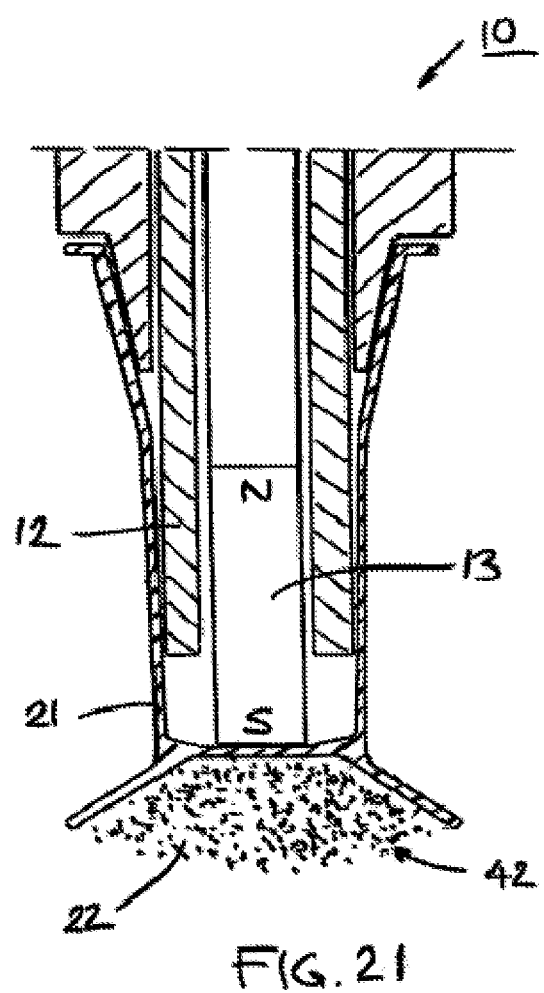
FIG. 21 presents a partially sectioned side view of yet another embodiment of the magnet unit equipped with another kind of a protective membrane.

FIG. 21 presents another magnet unit 10 that includes a longitudinally magnetized magnet 13, a ferromagnetic sleeve 12 a and protective membrane 21 that has a pocket 42 at its end for micro particles 22. By means of such a structure a large amount of particles 22 may be collected, which particles do not easily get released from the surface of the protective membrane 21 during the transfer.

Figure 22:
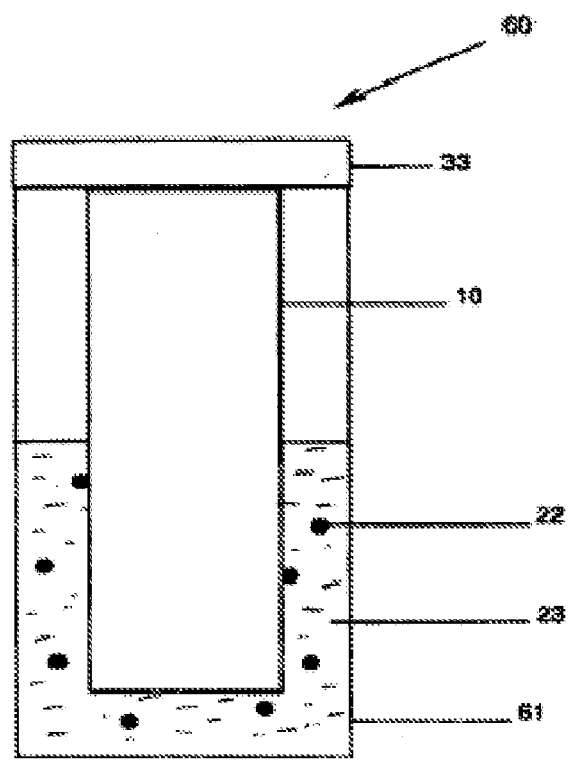

FIG. 22 presents in a general manner a reactor unit 60 according to the invention that includes in its simple form a reactor vessel 61 and a lid 33, by means of which the reactor vessel 61 may be closed to the reactor unit 60. The reactor vessel 61 contains liquid 23 needed for the process, which liquid contains liquid needed for the process, such as culture media, sample, buffer solution and micro particles 22. The magnet unit 10 is in this embodiment connected to the lid 33 of the reactor vessel 61, which lid simultaneously acts as a flange joint for the magnet unit 10. At simplest the magnet in the magnet unit 10, included in the reactor unit 60, is merely a magnet that has no protective membrane. According to the previously presented and other embodiments the magnet may however be coated with a protective coating or there may be a separate shield or protective membrane consisting of elastomer or non-elastomer material in connection to the magnet.

The above-mentioned embodiments serve only as examples of applying the idea according to the invention. It is evident for those skilled in the art that various embodiments may exist within the scope of the claims that follow farther behind.

LIST OF REFERENCES 10 magnet unit
12 ferromagnetic tube or sleeve
13 magnet
21 protective membrane
22 micro particles
23 solution
25 liquid surface
26 vessel
28 rotational axis
29 ridge of the protective membrane
40 multi-channel transfer device for micro particles
41 group of magnet units
42 pocket
60 reactor unit
61 reactor vessel
62 channel
63 valve
64 tip
70 environmental cabinet
71 motor
72 drive mechanism
73 narrowing
74 compartment
75 elastic element

The invention claimed is:

1. A magnetic enrichment method comprising:
   (a) placing micro particles (22) that bind to a biological component, into a solution (23) comprising the biological component, in a reactor vessel (26);
   (b) allowing the micro particles (22) to bind to the biological component in the solution (23) in a closed reactor unit (60) under controlled conditions, wherein the closed reactor unit (60) comprises a magnetic unit (10) comprising at least one magnet (13), a ferromagnetic tube (12), and the reactor vessel (26), wherein conditions in the closed reactor unit (60) are controllable and wherein the at least one magnet (13) and the ferromagnetic tube (12) can each be moved in relation to each other in order to adjust the magnetic field strength of the at least one magnet;
   (c) using the magnetic unit (10) to collect the biological component bound to the micro articles (22) in the solution (23) in the closed reactor unit (60); and
   (d) enriching the biological component by releasing the component into another solution,
   wherein the micro particles are magnetic.

2. The method according to claim 1, wherein enriching the biological component comprises:
   opening the closed reactor unit (60);
   removing the collected micro particles (22) from the reactor vessel (26) with the magnet unit (10); and
   releasing the collected micro particles (22) into a solution of another vessel.

3. A method for magnetic binding of a biological component, comprising:
   (a) in a reactor vessel (26), placing micro particles (22) having an enzymatic activity and/or binding properties into a solution (23) comprising a biological component;
   (b) mixing the micro particles (22) in the solution (23) in a closed reactor unit (60), wherein the closed reactor unit (60) comprises a magnetic unit (10) comprising at least one magnet (13), a ferromagnetic tube (12) and the reactor vessel (26) and
   wherein the at least one magnet (13) and the ferromagnetic tube (12) can each be moved in relation to each other in order to adjust the magnetic field strength of the at least one magnet;
   (c) carrying out a binding reaction in the closed reactor unit (60), thereby binding the biological component to the micro particles;
   (d) using the magnet unit (10) to collect the micro particles (22) from the solution (23);
   (e) opening the closed reactor unit (60);
   (f) removing the micro particles (22) from the reactor vessel (26) with the magnet unit (10); and
   (g) transferring the micro particles (22) into a solution in another vessel,
   wherein the micro particles are magnetic.

4. The method according to claim 1 or claim 3, wherein the micro particles (22) in the closed reactor unit (60) form a thin layer over the magnet unit (10); over a protective membrane (21) of the magnet unit (10); or on the inner surface of the closed reactor unit (60) by a magnet (13) placed outside the closed reactor unit (60).

5. The method according to claim 1 or claim 3, wherein the closed reactor unit (60) comprises channels (62) for rotating solution (23) in and out of the reactor unit (60); for adding sample into or removing sample from the closed reactor unit (60); for controlling gases or liquid added into the closed reactor unit (60), controlling pH value in the closed reactor unit (60) and controlling salt content in the closed reactor unit (60); or for filtering gases or liquid added into the closed reactor unit (60).

6. The method according to claim 1 or claim 3, wherein several closed reactor units (60) are placed in an environmental cabinet (70), wherein the environmental cabinet controls the temperatures of the closed reactor units (60), rotation speeds of the magnets (13), gas exchange, sampling and additions of samples or solutions (23) into the closed reactor units (60).

7. The method according to claim 1 or claim 3, wherein the magnet unit (10) of the closed reactor unit (60) is released from the reactor vessel (26), and the micro particles (22) and biological components bound to micro particles (22) are washed and enriched in separate vessels from the reactor vessel (26).

8. The method according to claim 1 or claim 3, wherein the solution (23) and the micro particles (22) in the closed reactor unit (60) are mixed by movement of projections or depressions inside the outer surface of the reactor vessel (26).

9. The method according to claim 1 or claim 3, wherein efficient movement of the solution (23) inside the closed reactor unit (60) is provided by directing the solution (23) between the micro particles (22); by directing the solution (23) as a flow passing the magnet unit (10); by moving the magnet unit (10) in relation to the walls of the reactor vessel (26) to mix the solution (23); by moving the walls of the reactor vessel (26) in relation to the magnet unit (10) to mix the solution (23); or by pumping the solution (23) inside the closed reactor unit (60).

10. The method according to claim 1 or claim 3, wherein the solution (23) is directed to pass a narrowing (73) between the reactor vessel (26) and the magnet unit (10), in the middle of the closed reactor unit (60), by rotating the closed reactor unit (60) around its longitudinal axis or by rocking the closed reactor unit (60).

11. The method according to claim 1 or claim 3, wherein the solution (23) is mixed by movement of a flexible element (75) in the magnet unit (10).

12. The method according to claim 1 or claim 3, wherein the reactor vessel (26) comprises a stretchy material, and wherein the solution (23) is mixed by pushing the bottom of the reactor vessel (26) downwards.

13. The method according to claim 1 or claim 3, wherein any of the following are bound to the surface of the micro particle (22): protein, antibody, peptide, enzyme, Protein A, Protein G, avidin, streptavidin, biotin, Cibacron blue, proteamine, pepstatin, PEG, lysine, BSA, NTA, EDTA, IDA, polysaccharide, lectin, one- or two-stranded nucleotide sequence, DNA, RNA, mRNA, LNA, PNA, bacteria, virus, yeast or cell.

14. The method according to claim 1 or claim 3, wherein the micro particles (22) bound to the biological component, are further used to carry out chromatographic purification.

15. The method of claim 14, wherein chromatographic purification is selected from the group consisting of: ion exchange chromatography, reverse phase chromatography, hydrophobic chromatography and affinity chromatography.

16. The method according to claim 1 or claim 3, wherein the micro particles (22) bound to the biological component, are further used to isolate or enrich biological components selected from the group consisting of: pathological bacteria, viruses, parasites, or protozoans.

17. The method of claim 16, wherein the pathological bacteria are selected from the group consisting of *Salmonella, Listeria, Escherichia coli* O157 and *Clostridium*.

18. The method according to claim 1 or claim 3, wherein the micro particles (22) bound to the biological component, are further used to purify a biological component selected from the group consisting of: DNA, RNA, mRNA, proteins, peptides, cells or cell organelles.

19. The method of claim 1 or claim 3, wherein the magnetizing axis of the at least one magnet is transverse in relation to the longitudinal axis of the ferromagnetic tube.

* * * * *